United States Patent
Lackey et al.

(10) Patent No.: US 7,783,344 B2
(45) Date of Patent: Aug. 24, 2010

(54) HYDRATION MONITORING

(75) Inventors: Robert P. Lackey, Carlsbad, CA (US); Darrel Drinan, San Diego, CA (US); Carl F. Edman, San Diego, CA (US)

(73) Assignee: PhiloMetron, Inc., San Diego, CA (US)

( * ) Notice: Subject to any disclaimer, the term of this patent is extended or adjusted under 35 U.S.C. 154(b) by 129 days.

(21) Appl. No.: 10/922,370

(22) Filed: Aug. 20, 2004

(65) Prior Publication Data

US 2005/0070778 A1 Mar. 31, 2005

Related U.S. Application Data

(60) Provisional application No. 60/496,558, filed on Aug. 20, 2003, provisional application No. 60/570,852, filed on May 13, 2004.

(51) Int. Cl.
*A61B 5/05* (2006.01)
(52) U.S. Cl. ..................................................... 600/547
(58) Field of Classification Search .................. 600/547
See application file for complete search history.

(56) References Cited

U.S. PATENT DOCUMENTS

| | | | |
|---|---|---|---|
| 4,860,753 A * | 8/1989 | Amerena | 600/306 |
| 4,966,158 A * | 10/1990 | Honma et al. | 600/547 |
| 5,086,781 A | 2/1992 | Bookspan | |
| 5,297,556 A * | 3/1994 | Shankar | 600/481 |
| 5,335,667 A * | 8/1994 | Cha et al. | 600/547 |
| 5,732,710 A * | 3/1998 | Rabinovich et al. | 600/547 |
| 5,738,107 A | 4/1998 | Martinsen et al. | |
| 5,749,369 A * | 5/1998 | Rabinovich et al. | 600/547 |
| 5,788,643 A | 8/1998 | Feldman | |
| 6,047,203 A | 4/2000 | Sackner et al. | |
| 6,125,297 A | 9/2000 | Siconolfi | |
| 6,339,722 B1 | 1/2002 | Heethaar et al. | |
| 6,370,426 B1 * | 4/2002 | Campbell et al. | 600/547 |
| 6,459,930 B1 | 10/2002 | Takehara et al. | |
| 6,524,239 B1 * | 2/2003 | Reed et al. | 600/300 |
| 6,551,252 B2 | 4/2003 | Sackner et al. | |
| 6,595,929 B2 | 7/2003 | Stivoric et al. | |
| 6,615,077 B1 * | 9/2003 | Zhu et al. | 600/547 |
| 6,714,813 B2 | 3/2004 | Ishigooka et al. | |
| 6,790,178 B1 | 9/2004 | Mault et al. | |
| 6,980,852 B2 * | 12/2005 | Jersey-Willuhn et al. | 600/547 |
| 7,184,820 B2 * | 2/2007 | Jersey-Willuhn et al. | 600/547 |

(Continued)

FOREIGN PATENT DOCUMENTS

WO WO 03/015005 A2 2/2003

OTHER PUBLICATIONS

International Preliminary Report on Patentability dated Mar. 2, 2006.

*Primary Examiner*—Max Hindenburg
*Assistant Examiner*—Jeffrey G Hoekstra
(74) *Attorney, Agent, or Firm*—Knobbe Martens Olson & Bear LLP

(57) ABSTRACT

Systems and techniques for monitoring hydration. In one implementation, a method includes measuring an electrical impedance of a region of a subject to generate an impedance measurement result, and wirelessly transmitting the data to a remote apparatus. The probe with which impedance is measured may take the form of a patch adhesively secured to the subject.

24 Claims, 11 Drawing Sheets

U.S. PATENT DOCUMENTS

| | | | |
|---|---|---|---|
| 7,191,000 B2 * | 3/2007 | Zhu et al. ............... 607/9 |
| 2002/0045836 A1 * | 4/2002 | Alkawwas ............ 600/509 |
| 2003/0004403 A1 * | 1/2003 | Drinan et al. ......... 600/301 |
| 2003/0120170 A1 | 6/2003 | Zhu et al. |
| 2004/0030258 A1 | 2/2004 | Williams et al. |
| 2004/0171962 A1 | 9/2004 | Leveque et al. |
| 2006/0058593 A1 | 3/2006 | Drinan et al. |
| 2006/0264775 A1 | 11/2006 | Mills et al. |

* cited by examiner

HYDRATION MONITORING

CROSS-REFERENCE TO RELATED APPLICATIONS

This application claims priority to U.S. Provisional Application Ser. No. 60/496,558 filed Aug. 20, 2003 and entitled "METHOD AND APPARATUS FOR MONITORING PULMONARY EDEMA USING BIOIMPEDANCE" and the priority of U.S. Provisional Application Ser. No. 60/570,852 filed May 13, 2004 and entitled "METHOD AND APPARATUS FOR AMBULATORY HYDRATION MONITORING," the contents of both of which are incorporated herein by reference.

BACKGROUND

This disclosure relates to monitoring the hydration of organisms.

Many species of organisms are largely water. The amount and/or disposition of water in an individual organism (i.e., the hydration of the organism) is often correlated with the health of the individual organism. For example, an excess or a scarcity of water can be indicative of acute and/or chronic disease states.

One example of such an acute disease state is acute dehydration. Dehydration is the excessive depletion of body water. There are a number of causes of acute dehydration including heat exposure, prolonged vigorous exercise, and diuretics. For example, the US Air Force Field Manual (FM 3-04.301-Aeromedical Training for Flight Personnel) describes that when ambient temperature is increased above 82-84° F., sweat production by humans increases abruptly and dehydration may result. Humidity can also impact sweat production and lead to dehydration. For example, with 115° F. and 10% humidity, a human can function normally with water and salt replenishment. However when humidity is 80%, the same person can become incapacitated within 30 minutes at 115° F. due to excessive depletion of body water.

One example of a chronic disease state associated with an excess of water is pulmonary edema. Pulmonary edema is the extravascular accumulation of fluid in the lungs. There are a number of causes of pulmonary edema including mitral stenosis or left ventricular failure. Pulmonary edema can be associated with congestive heart failure.

Another example of such a chronic disease state is hyperhydration. Hyperhydration is a state in which the body includes an excessive amount of water. In patients undergoing kidney dialysis, hyperhydration may lead to hypertension and increased mortality.

SUMMARY

Accordingly, this disclosure describes systems and techniques for monitoring the hydration of an organism. Hydration can be monitored, e.g., to identify dehydration or other disease state of the organism.

In one implementation, a device includes a portable hydration monitoring probe dimensioned to be continuously borne by an organism. The probe includes a supply of electrical power, an electrode to exchange electrical energy from the supply with a local portion of the organism bearing the probe, a controller to generate data representing a result of the hydration monitoring, the result reflecting a local bioelectric impedance based on the exchange of electrical energy at the electrode, and a data communication device configured to wirelessly communicate the data representing the hydration monitoring result to a remote apparatus.

This and other implementations can include one or more of the following features. The portable hydration monitoring probe can include a patch probe.

These and other systems and techniques can be implemented to realize one or more of the following advantages. Hydration can be monitored to identify a variety of disease states. Monitoring can be long term, using portable probes dimensioned to be borne by the monitored organism. The impact of skin surface temperature on hydration measurements can be considered when analyzing hydration monitoring results. Hydration monitoring results can be communicated using wireless communication links that do not hinder the mobility of ambulatory subjects.

DETAILED DESCRIPTION

Figure 1:
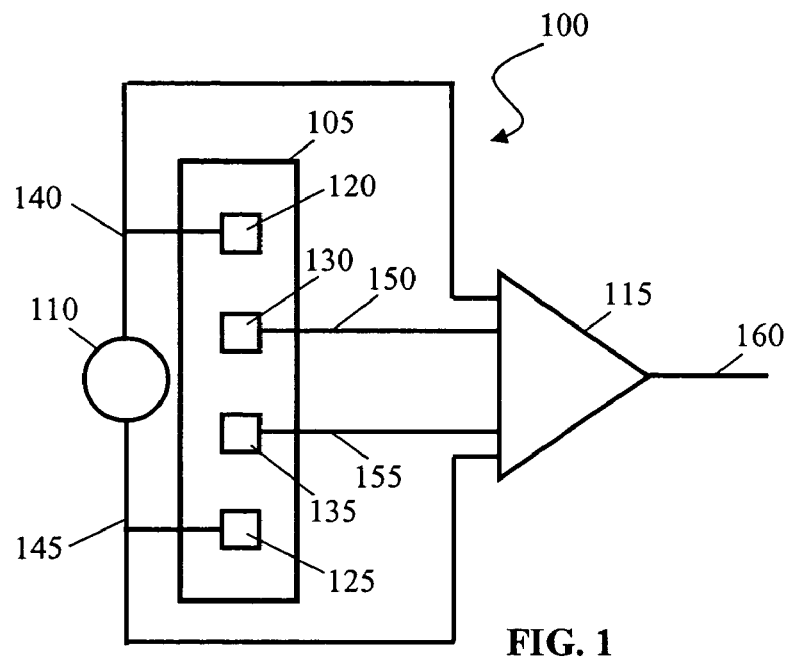
FIG. 1 shows a probe for monitoring the hydration of an organism.

FIG. 1 shows a probe 100 for monitoring the hydration of an organism. Probe 100 includes a body 105, an energy source 110, and a sensing circuit 115. Body 105 can be a flexible member in that it can be contoured to follow the skin surface or other portion of an organism, such as, for example, a patch or strap. Body 105 supports probe/organism interfaces 120, 125, 130, 135 which apply or exchange energy with the subject and which sense energy exchange parameters in a way to measure the impedance of a region of the subject. In most embodiments, interfaces 120, 125 130, 135 will be electrodes adapted to exchange electrical energy with a human, although some optical element adapted to illuminate a human may also be possible. Typically, two of the interfaces 120, 125 are used to force current flow from one point on the subject to a second point on the subject. The other two interfaces 130, 135 are used to measure the voltage across two points on the subject. It may be noted that the current application points and the voltage measurement points in these embodiments can be the same, adjacent to one another, or at significantly different locations.

Energy source 110 can be, e.g., an optical energy source or an electric energy source. For example, energy source can be an alternating and/or direct current and/or voltage source. Energy source 110 is connected to inputs 120, 125 by leads 140, 145. Leads 140, 145 can conduct energy generated by source 110 for exchange with the portion of the organism coupled to main body 105. For example, leads 140, 145 can be electrical wires capable of carrying an electric current for exchange with the portion of the organism, or leads 140, 145 can be optical waveguides capable of carrying light for exchange with the portion of the organism followed by main body 105.

In one electrical embodiment, a sensing circuit 115 comprises a differential amplifier connected to electrodes 120, 125 by leads 140, 145 and to electrodes 130, 135 by leads 150, 155. Leads 140, 145 can conduct voltage across source 110 to amplifier 115. Leads 150, 155 can conduct voltage across electrodes 130, 135 as another input to the amplifier 115. Amplifier 115 can sense voltages across electrodes 130, 135 and electrodes 120, 125 to generate one or more results 160. It will be appreciated that amplifier 115 could be implemented as two or more amplifiers that separately sense relative voltages across any desired electrode pairs. Current sensing could also be implemented to directly measure the current output from source 110.

In operation, main body 105 flexes to follow a portion of an organism and maintain inputs 120, 125 and outputs 130, 135 so that they can exchange energy with the followed portion. Source 110 generates one or more types of energy that is conducted over leads 140, 145 through interfaces 120, 125 and exchanged with the followed portion of the organism. In turn, interfaces 130, 135 sense one or more energy exchange parameters from the followed portion. Sensing circuit 115 generates a result 160 based on the sensed signals. Result 160 reflects, at least in part, the hydration of the monitored organism.

Probe 100 can generate result(s) 160 continuously or intermittently over extended periods of time. For example, result 160 can be a subset of the comparisons of the sensed parameters at interfaces 130, 135 with the amount of energy input at inputs 120, 125, or result 160 can be all such comparisons. For example, result 160 can be intermittent samples of voltages from the results of continuous application of a substantially constant current. As another example, result 160 can be periodic (e.g., every 5 to 30 minutes, such as every 10 minutes) results of successive, shorter duration current applications.

Figure 2:
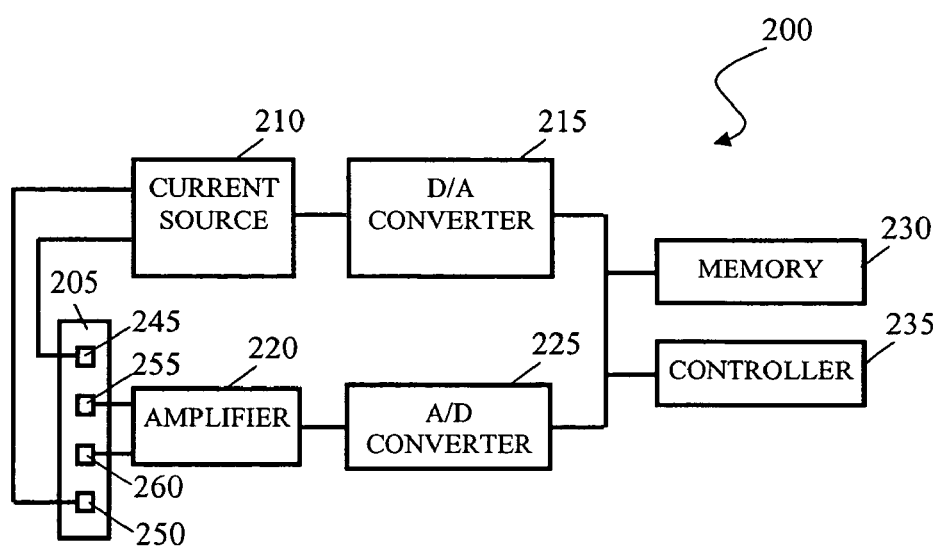
FIG. 2 shows a bioelectric impedance spectroscopy probe for monitoring the hydration of an organism.

FIG. 2 shows one implementation of a probe for monitoring the hydration of an organism, namely a bioelectric impedance spectroscopy probe 200. Bioelectric impedance spectroscopy is a measurement technique in which the electrical conductivity of all or a portion of an organism is measured. When the conductivity of the entirety of an organism is measured such as by passing current from one ankle to an opposite wrist or between both hands, this can be referred to as whole body bioelectric impedance spectroscopy. When the conductivity of a portion of an organism is measured such as by a cluster of more locally placed electrodes, this can be referred to as segmental (or regional) bioelectric impedance spectroscopy. In either case, the measured electrical conductivity can reflect the hydration of the measured organism or the measured portion of the organism.

Bioelectric impedance spectroscopy generally involves the exchange of electrical energy with the organism. The exchanged electrical energy can include both alternating current and/or voltage and direct current and/or voltage. The exchanged electrical energy can include alternating currents and/or voltages that alternate at one or more frequencies. For example, the alternating currents and/or voltages can alternate at one or more frequencies between 100 Hz and 1 MHz, preferably at one or more frequencies between 5 KHz and 250 KHz.

Different frequencies of electrical energy can be used to measure conductivity in different portions of the organism. For example, in some organisms, lower frequency electrical energy may be conducted preferentially through tissues having fewer membranous components whereas higher frequencies may be conducted through a larger variety of tissues. In many cases, it is advantageous to make impedance measurements at two or more different frequencies in the same region. As explained further below, DC measurements can help characterize impedance over the skin surface. Thus, measurements at different frequencies made by a single probe can provide information regarding both the amount and disposition of water within a probed organism or within a probed portion of the organism.

Referring again to FIG. 2, bioelectric impedance spectroscopy probe 200 includes a body 205, a current source 210, a digital-to-analog converter 215, an amplifier 220, an analog-to-digital converter 225, a memory 230, and a controller 235. Body 205 is a flexible member that supports two working electrodes 245, 250 and two sensing electrodes 255, 260. Body 205 can be flexible enough to follow a portion of the human body to maintain electrodes 245, 250, 255, 260 in contact with that portion. The followed portion can include skin surfaces, mucosal surfaces in the mouth and/or nasal passages, and other body passages or orifices. Body 205 can be sized to probe the conductivity of the entirety of an organism and thus perform whole body bioelectric impedance spectroscopy. In some advantageous embodiments described in detail herein, body 205 is sized to probe the conductivity of a portion of an organism and thus perform segmental bioelectric impedance spectroscopy.

Working electrodes 245, 250 can be adapted to conduct current through or along the probed portion of the monitored organism. Sensing electrodes 255, 260 can be adapted to measure the potential of locations in the probed portion of the monitored organism. Electrodes 245, 250, 255, 260 are generally electrically conductive in that their electrical impedance is relatively small when compared to the electrical impedance of the monitored portion of an organism at the probed frequency. For example, electrodes 245, 250, 255, 260 can include metals, sintered metallic composites, conductive polymers, gels, carbon-based materials, silicon materials, electrically conductive microneedles, conductive solutions, or combinations thereof. In one implementation, electrodes 245, 250, 255, 260 are electrically conductive adhesive gel electrodes such as the RED DOT electrodes available from 3M Corp. (St. Paul, Minn.).

Electrodes 245, 250, 255, 260 can be supported by body 205 on the outer surface of the skin of a monitored organism. Alternatively, electrodes 245, 250, 255, 260 can be supported by body 205 beneath the skin of a monitored organism. For example, electrodes 245, 250, 255, 260 can be supported subdermally or electrodes 245, 250, 255, 260 can be supported on transdermal elements such as microneedles that penetrate the skin. When placed on the skin surface, electrodes 245, 250, 255, 260 can advantageously be each supported by body 205 at positions that are separated from one another by more than approximately ten times the thickness of the skin. When hydration is monitored in humans, electrodes 245, 250, 255, 260 that are above the skin can each generally be supported at positions that are separated from one another by more than 2.5 millimeters. In one implementation, the distance between working electrodes 245, 250 is greater than 1 cm. For embodiments that include a localized cluster of electrodes on one or more patches secured to the skin, the distance between electrodes is advantageously less than about 25 cm so that the impedance measurement is focused regionally on the subject. Such regional measurements have been found to produce useful data that can be generated and distributed with convenient apparatus.

In one implementation, working electrodes 245, 250 are different than sensing electrodes 255, 260. For example, working electrodes 245, 250 can be larger than sensing electrodes 255, 260 and/or made from different materials.

Current source 210 is a source of alternating and/or direct electrical current. As deployed in probe 200, current source 210 can drive electrical current from working electrode 245 to working electrode 250 through and/or along a monitored organism. In one implementation, current source 210 is capable of driving between 10 microamperes and 10 milliamperes, preferably between 100 microamperes and 1 milliamperes, of one or more frequencies of alternating and/or direct current through or along electrical impedances characteristic of humans. Typically, current is held at a known or measured substantially constant value, and voltage is measured to provide an impedance value. It is also possible to apply a constant voltage and measure the amount of current. Digital-to-analog converter 215 can be an integrated circuit or other electronic device that converts a digital signal into a corresponding analog signal. As deployed in probe 200, digital-to-analog converter 215 can convert digital control signals from controller 235 into analog control signals to control the output of electrical current from current source 210.

Amplifier 220 can be a differential voltage amplifier in that it amplifies a voltage difference on sensing electrodes 255, 260. This voltage difference results from current source 210 driving electrical current from working electrode 245 to working electrode 250 through and/or along the monitored organism. Analog-to-digital converter 225 can be an integrated circuit or other electronic device that converts this sensed voltage difference into a corresponding digital signal for reading by controller 235 and/or storage in memory 230.

Memory 230 can be a data storage device that can retain information in machine-readable format. Memory 230 can be volatile and/or nonvolatile memory. For example, memory 230 can be a RAM device, a ROM device, and/or a memory disk.

Controller 235 is a device that manages the generation and flow of data in probe 200. Controller 235 can be hardware configured to perform select operations or a data processing device that performs operations in accordance with the logic of a set of machine-readable instructions. In some implementations, controller can receive information related to the management of the generation and flow of data in probe 200 via one or more input devices. In some implementations, controller 235 can output information from probe 200 via one or more output devices. Custom ASICs or gate arrays can be used, as well as commercially available microcontrollers from, for example, Texas Instruments and Motorola.

The operations performed by controller 235 can include regulating the timing of hydration measurements and the timing of the transmission of hydration measurement results, logic operations, signal processing, and data analysis. For example, data analysis can be used to determine the bioelectric impedance of portions of a monitored organism. For example, equivalent circuit impedance analysis in the time or frequency domain can be performed. Instructions for performing such operations can be stored in a read only memory portion of memory 230, temporary values generated during such operations can be stored in a random access portion of memory 230, and the results of operations can be stored in a non-volatile portion of memory 230.

In operation, current source 210 drives one or more frequencies of alternating and/or direct current between working electrodes 245, 250 and through the subject organism. Amplifier 220 buffers and amplifies the potential difference between sensing electrodes 255, 260. Analog-to-digital converter 225 converts this signal into a digital form that can be received by controller 235 for storage at memory 230, as appropriate. In some implementations, controller 235 may control source 210 to change the frequency and/or magnitude of current generated. The control of source 210 can be performed in light of the magnitude of the signal(s) output by amplifier 220 and/or in light of instructions received by controller 235 over one or more input devices.

Figure 3:
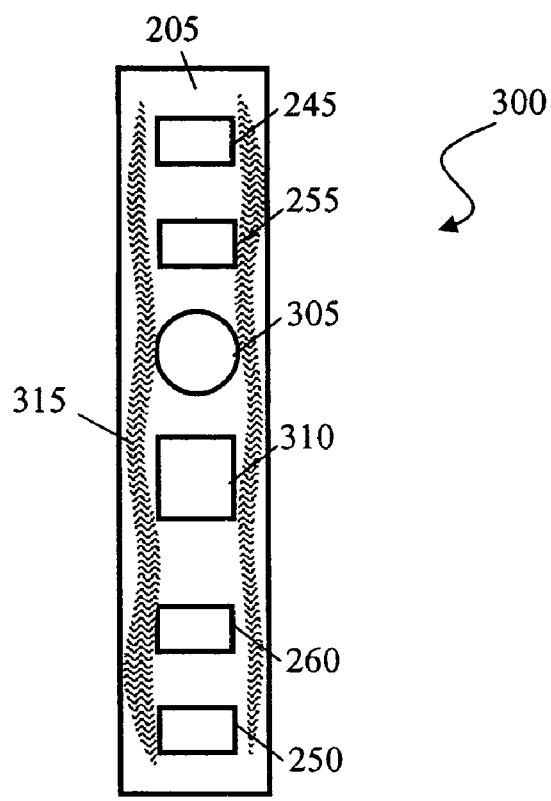
FIG. 3 shows a bandage bioelectric impedance spectroscopy probe.

FIG. 3 shows one implementation of a portable bioelectric impedance spectroscopy probe, namely a bandage (or "patch") probe 300. Probe 300 can be self-powered in that main body 205 includes (in addition to electrodes 245, 250, 255, 260) a portable power source, such as a battery 305. Probe 300 is portable in that probe 300 can be moved from a fixed location and is adapted to perform at least some of the signal generation and processing, control, and data storage functions of current source 210, a digital-to-analog converter 215, an amplifier 220, an analog-to-digital converter 225, a memory 230, and a controller 235 without input from a fixed device. For example, probe 300 can be borne by the monitored organism. Circuitry 310 can be, e.g., an application specific integrated circuit (ASIC) adapted to perform these functions. Circuitry 310 can also be a data processing device and/or one or more input/output devices, such as a data communication device.

Main body 205 also advantageously includes an adhesive 315. Adhesive 315 can be adapted to adhere to the skin surface of the monitored organism and thereby maintain electrodes 245, 250, 255, 260 in contact with the portion of an organism followed by main body 205.

A portable probe 300 allows a monitored organism to be ambulatory while hydration monitoring occurs. This allows for data collection to be extended beyond periods of confinement. Thus, hydration monitoring can be continued while an organism participates in various activities at different locations, over durations suitable for identifying the onset of disease states.

Figure 4A:
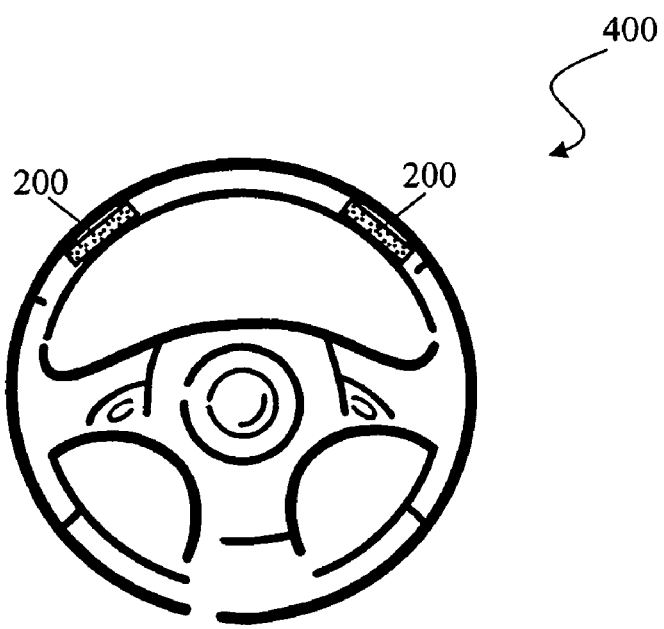
FIGS. 4A and 4B illustrate example deployments of a bioelectric impedance spectroscopy probe and a bandage probe to monitor hydration.
Figure 4B:
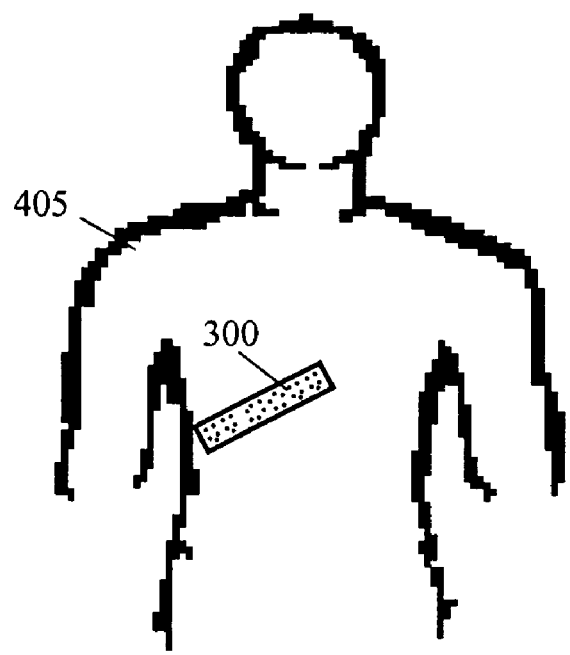

FIGS. 4A and 4B respectively illustrate example deployments of bioelectric impedance spectroscopy probe 200 and bandage probe 300 to monitor hydration. FIG. 4A shows a pair of probes 200 deployed along a steering wheel 400 so that a driver's hands will come into intermittent electrical contact with one or both of probes 200. During this intermittent contact, the driver's hydration can be monitored.

FIG. 4B shows bandage probe 300 deployed to adhere to the torso of person 405. Bandage probe 300 is sized to probe the conductivity of a portion of person 405. In particular, bandage probe 300 adheres to the front chest of person 405 with one end located in the vicinity of the xiphoid process. Bandage probe 300 extends axially and downward from the xiphoid process towards the lateral side of person 405.

This positioning of bandage probe 300 may facilitate the monitoring of hydration in the underlying tissue and lung, as well as the identification of disease states such as pulmonary edema.

Figure 5:
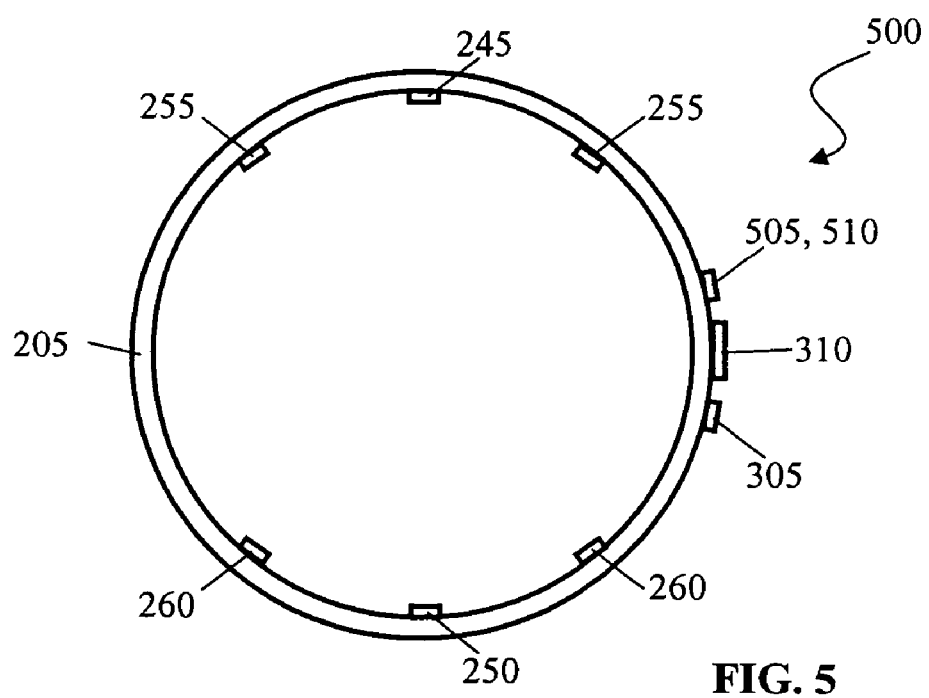
FIGS. 5 and 6 show a portable strap bioelectric impedance spectroscopy probe.
Figure 6:
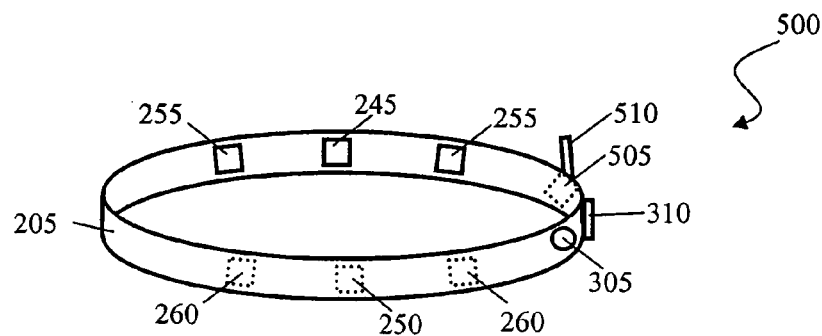

FIGS. 5 and 6 show another implementation of a bioelectric impedance spectroscopy probe, namely a portable strap probe 500. Main body 205 of strap probe 500 is a strap or a belt that can form a loop to encircle the body, or a portion of the body, of a monitored individual. Such an encirclement can maintain electrodes 245, 250, 255, 260 in contact with the encircled portion. In addition to working electrodes 245, 250, two sets of sensing electrodes 255, 260, battery 305, and circuitry 310, main body 205 also includes a data communication device 505 having a transceiver 510. Data communication device 505 can be a wireless communication device that can exchange information between circuitry 310 and an external entity. Wireless data link 1125 can carry information using any of a number of different signal types including electromagnetic radiation, electrical signals, or acoustic signals. For example, data communication device 505 can be a radio frequency communication device. Transceiver 510 can be an assembly of components for the wireless transmission and reception of information. The components can include, e.g., an RF antenna. The wireless receiver/transmitter circuitry can be made part of any embodiment described herein.

The two sets of sensing electrodes 255, 260 can be used to measure hydration at different locations on a monitored individual. For example, when working electrodes 245, 250 drive current through and/or along the surface of the encircled portion of a monitored individual, the potential differences between all sensing electrodes 255, 260 can be used to gain information about the conduction of current in the vicinity of electrodes 255, 260. A measurement of multiple potential differences between more than two sensing electrodes 255, 260 can also be used, e.g., to make cross measurements and ratiometric comparisons that can be used to monitor hydration while aiding in calibration and helping to account for measurement variability such as temperature changes, changes in the position of the monitored individual, and movement of strap probe 500 over time.

Figure 7:
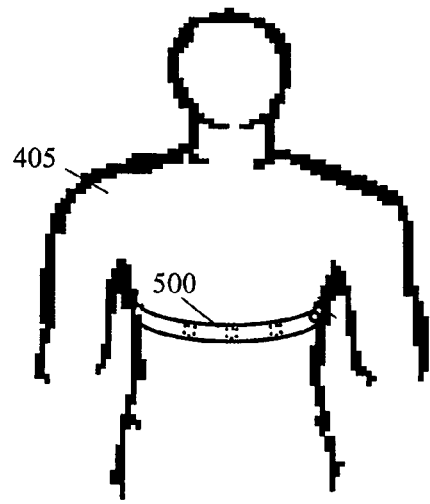
FIGS. 7, 8A, 8B, 8C, 9A, and 9B illustrate example deployments of a strap probe to monitor hydration.

FIGS. 7, 8A, 8B, 9A, and 9B illustrate example deployments of implementations of strap probe 500 to monitor hydration in a person 405. In FIG. 7, strap probe 500 is sized to encircle the torso of person 405 and is deployed to probe the conductivity of the torso of person 405. Such a positioning of strap probe 500 may facilitate the monitoring of hydration in the underlying tissue and lung, as well as the identification of disease states such as pulmonary edema.

Figure 8A:
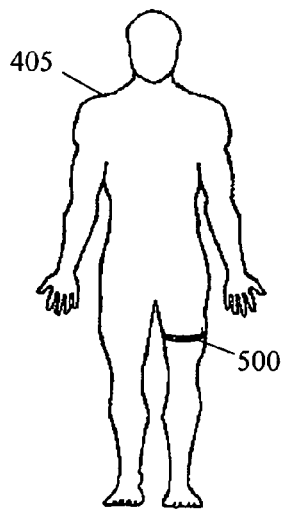

In FIG. 8A, strap probe 500 is sized to encircle the thigh of person 405 and is deployed to probe the conductivity of the thigh of person 405. Such a positioning of strap probe 500 may facilitate the monitoring of hydration in the underlying tissue, as well as the identification of disease states such as acute or chronic dehydration.

Figure 8B:
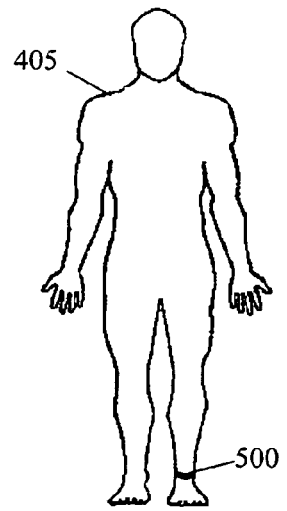

In FIG. 8B, strap probe 500 is sized to encircle the lower leg of person 405 and is deployed to probe the conductivity of the lower leg of person 405. As shown, strap probe 500 encircles the ankle, but strap probe 500 can also encircle the foot, the calf, or a toe to probe the conductivity of the lower leg. Such a positioning of strap probe 500 may facilitate the monitoring of hydration in the underlying tissue, as well as the identification of disease states such as congestive heart failure where water accumulates in the lower legs.

Figure 8C:
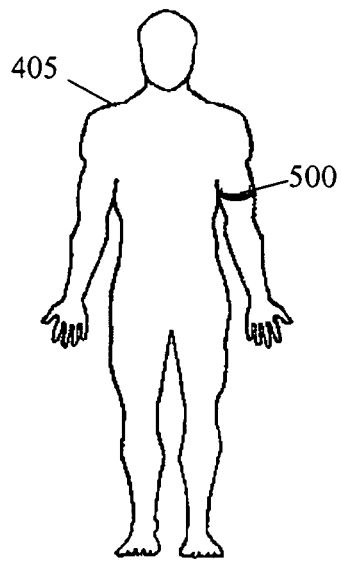

In FIG. 8C, strap probe 500 is sized to encircle the bicep of person 405 and is deployed to probe the conductivity of the bicep of person 405. Such a positioning of strap probe 500 may facilitate the monitoring of hydration in the underlying tissue, as well as the identification of disease states such as acute or chronic dehydration.

Figure 9A:
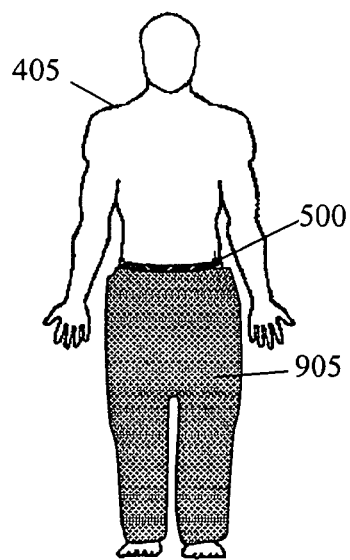

In FIG. 9A, strap probe 500 is incorporated into a pair of pants 905 and sized to encircle the torso of person 405 to probe the conductivity of the torso of person 405. Incorporating a probe 500 into pants 905 may reduce the intrusiveness of probe 500 and help ensure that a monitored individual deploys probe 500.

Figure 9B:
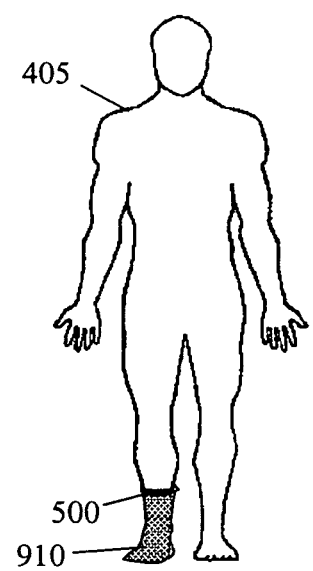

In FIG. 9B, strap probe 500 is incorporated into a sock 910 and sized to encircle the lower leg of person 405 to probe the conductivity of the lower leg of person 405. Incorporating a probe 500 into sock 910 may reduce the intrusiveness of probe 500 and help ensure that a monitored individual deploys probe 500.

As discussed further below, in some deployments, multiple probes at different locations may be used to monitor the hydration of a single individual. The measurement results from the different probes can be compared and correlated for calibration and error minimization. Other techniques that measure biological parameters can also be used in conjunction with single or multiple probes. The biological parameter measurements can be compared and correlated with the probe measurements to calibrate the measurements and minimize the error associated with the measurements. As one example, bioelectric impedance measurements made using a QUANTUM X body composition analyzer (RJL Systems, Inc., Clinton Twp., MI) and/or a Hydra 4200 bioimpedance analyzer (Xitron Technologies Inc., San Diego, Calif.) can be compared and correlated with probe measurements.

As another example, skin temperature measurements can be used in monitoring the hydration of an individual. In general, skin surface temperature will change with changes in blood flow in the vicinity of the skin surface of an organism. Such changes in blood flow can occur for a number of reasons, including thermal regulation, conservation of blood volume, and hormonal changes. In one implementation, skin surface measurements are made in conjunction with hydration monitoring so that changes in apparent hydration levels, due to such changes in blood flow, can be considered.

In some deployments, one or more probes can be moved to different portions of a single individual over time to monitor the hydration of the individual. For example, a probe can monitor the hydration of an individual at a first location (e.g., the torso) for a select period (e.g., between about 1 to 14 days, or about 7 days), and then the same probe can be moved to a different location (e.g., the thigh) to monitor the hydration of the same individual for a subsequent time period. Such movement of a probe can extend the lifespan of a probe and increase the type of information gathered by the probe. Further, movement of the probe can minimize surface adhesion loss and any decrease in hygiene associated with the monitoring.

The movement of a probe such as probe 500 to a new location on the body, or the attachment of a new probe at a different location, may result in a change in baseline impedance measurements even when the hydration of the monitored organism has not changed. A baseline measurement is a standard response to hydration monitoring. The standard response can be indicative of the absence of a disease state or of the absence of progression in a disease state. Changes in the baseline impedance measurements can result from changes in factors unrelated to a disease state. For example, changes in the baseline impedance measurements can result from different skin thicknesses, body compositions, or other differences between two locations. Measurements made at the different locations can be normalized to account for such differences in baseline measurements. Such a normalization can include adjustments in gain and/or adjustments in offset. Gain adjustments may be based on the absolute value of the impedance measurement(s), the impedance difference(s) observed at the old and the new locations, or combinations thereof. Offset adjustments can generally be made after gain adjustments and can be based on absolute impedance values and/or other factors. Alternatively, analysis thresholds used to identify disease states can be adjusted.

In some implementations, the monitored individual may be placed in a non-ambulatory state (e.g., supine and resting) in order to acquire directly comparable baseline measurements at different locations. Multiple probes need not be attached to the same organism in order to normalize baseline measurements. For example, hydration measurement results obtained using a first probe at a first location can be stored and compared with hydration measurement results obtained later using a second probe at a second location. This can be done, e.g., when the time between the collection of the results at the first location and the collection of the results at the second location is relatively short, e.g., less than 1 hr. If the replacement patch is not attached to the patient within this period, comparison of bioelectric impedance values to other calibration standards, e.g., body weight and body weight change, urine specific gravity, blood osmolality, can also be used for such comparisons.

Figure 10A:
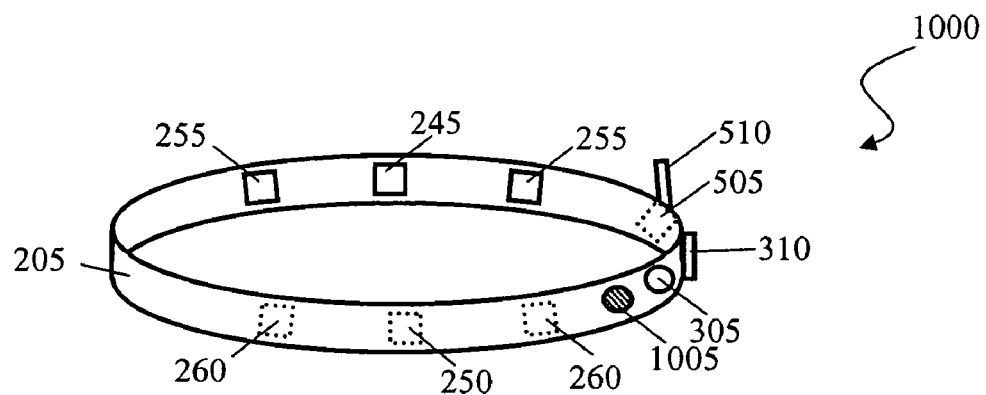
FIGS. 10A and 10B show other strap bioelectric impedance spectroscopy probes.

FIG. 10A shows another implementation of a strap probe, namely a strap probe 1000. In addition to electrodes 245, 250, 255, 260, battery 305, circuitry 310, data communication device 505, and transceiver 510, main body 205 also includes an output device 1005. Output device 1005 can be a visual display device (such as a light emitting diode or a liquid crystal display), an audio output device (such as a speaker or a whistle), or a mechanical output device (such as a vibrating element).

In operation, output device 1005 can present information regarding the hydration monitoring to a monitored individual. The presented information can be received by output device 1005 from circuitry 310 and can indicate monitoring results and/or alerts. Monitoring results can include the current hydration state of an individual as well as indications that certain disease states, such as acute dehydration, are present or imminent. Monitoring alerts can include indications of current or imminent apparatus malfunction, such as loss of contact between any of electrodes 245, 250, 255, 260 and the monitored individual, a lack of available memory, loss of a data communication link, or low battery levels.

Figure 10B:
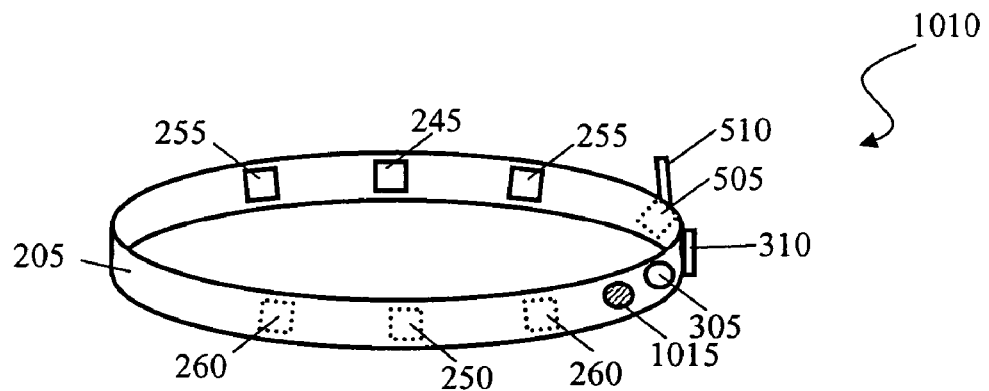

FIG. 10B shows another implementation of a strap probe, namely a strap probe 1010. In addition to electrodes 245, 250, 255, 260, battery 305, circuitry 310, data communication device 505, and transceiver 510, main body 205 also includes a skin temperature thermometer 1015. Thermometer 1015 can be a temperature sensing element that senses temperature in ranges encountered on the skin surface of the monitored organism. Thermometer 1015 can be, e.g., a thermister, a thermocouple, a mechanical thermometer, or other temperature-sensing device. This temperature sensor can be part of any probe embodiment described herein.

In operation, thermometer 1015 can present information regarding skin surface temperature to circuitry 310. The presented information can be used by circuitry 310 to perform data analysis and other aspects of hydration monitoring. Circuitry 310 can also transmit all or a portion of the temperature information to other devices using, e.g., data communication device 505 and transceiver 510.

With measurements of hydration and temperature at in the same vicinity of an organism, changes in apparent hydration levels due to changes in skin surface blood flow can be identified and accommodated in data analyses.

Figure 10C:
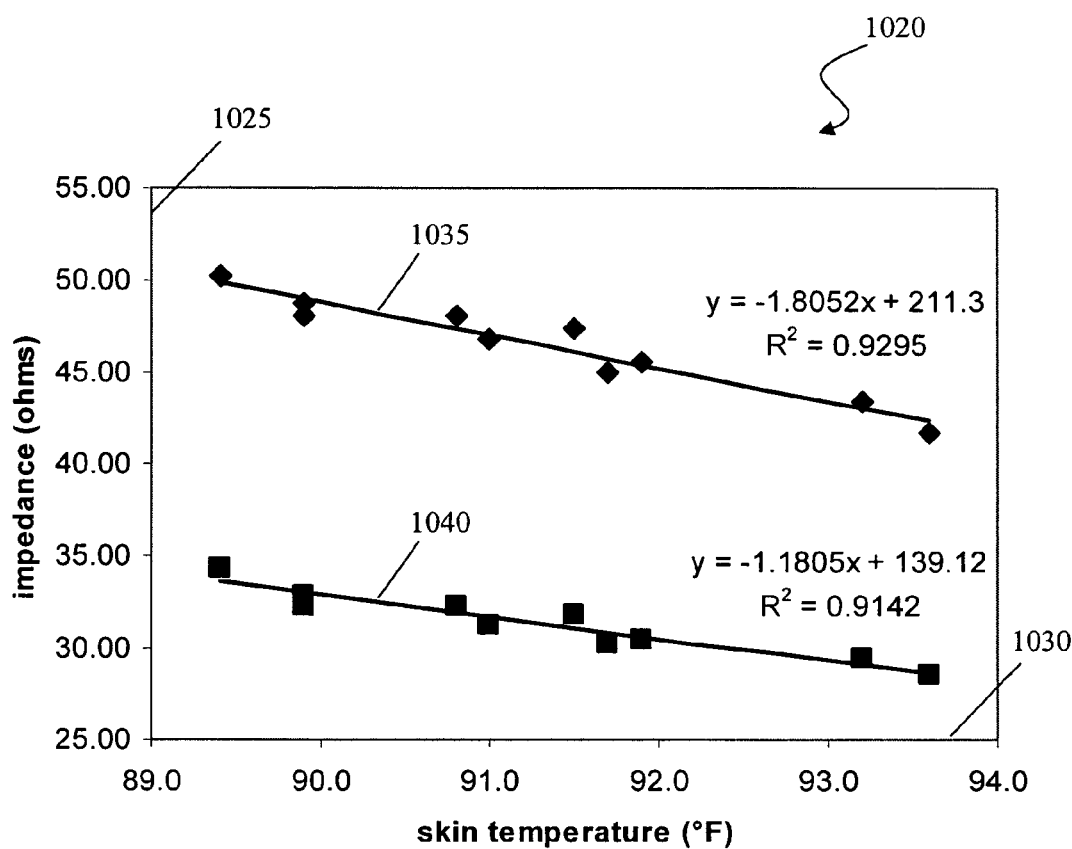
FIG. 10C shows a graph of example hydration monitoring results that can be obtained using a bioelectric impedance monitor and a skin temperature thermometer.

FIG. 10C shows a graph 1020 of example hydration monitoring results that were obtained using a bioelectric impedance monitor and a skin temperature thermometer. Graph 1020 shows the observed impedance 1025 of a region on the thigh of a monitored individual as a function of skin temperature 1030. Graph 1020 includes a pair of traces 1035, 1040. Trace 1035 shows the impedance measured with an electrical energy input signal having a frequency of 20 kHz, whereas trace 1040 shows the impedance measured with an electrical energy input signal having a frequency of 100 kHz.

Traces 1035, 1040 were obtained as follows. Four Red Dot electrodes (3M Corp., St. Paul, Minn.) were arrayed in a linear axial fashion upon the front of a thigh of a 42 yr old male subject weighing 201.3 pounds. The subject reclined in a supine position for 30 minutes in a room at ambient temperature (74° F.). The bioelectric impedance of the thigh at 20 kHz and 100 kHz was then measured with the subject in the supine position. The measured impedance of the thigh was 45.36 ohms at 20 kHz and 30.86 ohms at 100 kHz. The skin surface temperature of the thigh was then measured using an infrared thermometer (Thermoscan, Braun GmbH, Kronberg, Germany). The measured temperature was 89.0° F. The subject then jogged six miles, taking approximately 90 minutes. The subject was then weighed. The measured weight was 197.6 pounds, indicating a loss of body water of about 3.5 pounds, or about 1.7%. The subject then returned to the supine position in the ambient temperature room. The bioelectric impedance of the thigh at 20 kHz and 100 kHz was then measured periodically, as was skin surface temperature of the thigh.

Traces 1035, 1040 represent the results of these measurements. Initially, the measured bioelectric impedance at both 20 kHz and 100 kHz was lower than before jogging and the measured temperature was higher than before jogging. In other words, the measured bioelectric impedance at both 20 kHz and 100 kHz decreased as skin temperature in the vicinity of the bioelectric impedance measurement increased.

The observed changes in skin temperature are believed to result, at least in part, from local vasodilation as the body sheds excess heat generated during exercise. Such changes in vasodilation appear to decrease local impedance.

Over time, both the measured impedance and temperature moved in the direction of the values observed before jogging. The movement showed a linear relationship between measured impedance and measured skin temperature at both 20 kHz and 100 kHz. This relationship can be used to accommodate the impact of skin surface temperature on hydration monitoring results, as discussed further below. If desired, local vasodilation or vasoconstriction can be measured by other or additional methods such as with optical methods. A vasodilation parameter, whether measured or calculated via a temperature measurement or some other means may be used to correct absolute impedance measurements to appropriately determine impedance changes over time due to hydration changes.

At the end of the recovery period, the measured impedance of the thigh was 50.27 ohms at 20 kHz and 34.30 ohms at 100 kHz, for a net increase in impedance of 4.91 ohms (10.8%) at 20 KHz and 3.44 ohms (11.1%) at 100 KHz. Similar results have been observed with other subjects and other test conditions.

This approximately 11% net increase in measured bioelectric impedance at 20 kHz and 100 kHz is believed to reflect the water loss associated with the observed decrease in body weight (i.e., the decrease of about 1.7%).

The measurement results in traces 1035, 1040 can be used by circuitry 310 to perform data analysis and other aspects of hydration monitoring. For example, the impact of skin surface temperature on hydration monitoring results can be accommodated. In one example, the relationship between bioelectric impedance and temperature illustrated by traces 1035, 1040 can be used to compare hydration monitoring results obtained at different skin surface temperatures. For example, with a skin surface temperature of 90.5° F., the measured impedance at 20 kHz was 47.9 ohms. In order to compare this impedance measurement with impedance measurements made at a skin surface temperature of 89° F., the measured impedance can be adjusted by taking the difference between the two temperatures (i.e., 89° F.-90.5° F.) of −1.5° F. and multiplying this difference by the measured dependence of impedance at 20 kHz on temperature (i.e., the slope of −1.8052) to generate an adjustment value of 2.71 ohms. The adjustment value can be added to the impedance at 20 kHz measured with a skin surface temperature of 90.5° F. (i.e., 47.9+2.71) to yield an impedance that is comparable with impedance measurements made at 20 kHz with a skin surface temperature of 89° F. (i.e., 50.6 ohms). As seen, this adjusted impedance is consistent with the impedance actually measured at this skin surface temperature (i.e., 50.27 ohms).

Such combinations of skin surface temperature measurements and hydration monitoring results can be used to improve hydration monitoring. For example, bioelectric impedance measurements can be adjusted based on local skin surface temperature measurements made in the vicinity of the probe. This can improve the predictive value of impedance measurements, even relative to whole body impedance measurements where impedance measurement that reflect the electrical impedance through the entire body may not precisely correlate with temperature measurements made at one or two body locations.

Factors unrelated to hydration may influence local skin surface temperature measurements. These factors include the rate of convective cooling, the wind velocity, the presence of thermal insulation such as clothing, and ambient temperature gradients. Such factors that tend to influence heat exchange between the portion of the body of interest and the environment may be accounted for directly (e.g., using additional temperature or humidity sensors) or indirectly (e.g., using standard tables and known values applied to parameters such as the thickness of insulating clothing). The accounting for such factors can include adjustments to the local temperature used to compare hydration monitoring results.

In some implementations, hydration monitoring results obtained at portions of a monitored organism that have a known temperature relationship with another portion where skin surface measurement(s) are made can be adjusted based on that known relationship. Also, other factors including weight, height, age, general fitness level, degree of exertion, time of day, stage in a hormonal cycle, and gender can also be used to adjust hydration monitoring results and improve the predictive value of such results.

Figure 11:
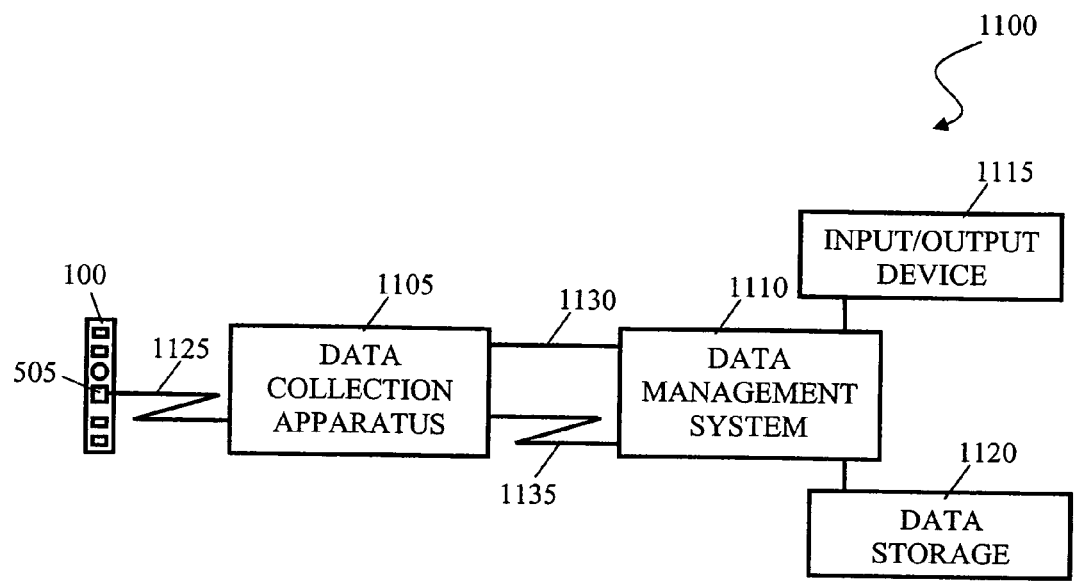
FIG. 11 shows a system for monitoring the hydration of an organism.

FIG. 11 shows a system 1100 for monitoring the hydration of an organism. System 1100 includes one or more probes 100 along with one or more data collection apparatus 1105, a data management system 1110, an input/output device 1115, and a data storage device 1120. Probe 100 includes a wireless data communication device 505 that is capable of establishing a wireless data link 1125 with data collection apparatus 1105. Wireless data link 1125 can transmit data using any of a number of different signals including electromagnetic radiation, electrical signals, and/or acoustic signals. When probe 100 is subdermal, data link 1125 can be a transdermal link in that data link 1125 conducts data along a path through the skin.

The data communicated along wireless data link 1125 can include a probe identifier. A probe identifier is information that identifies probe 100. Probe 100 can be identified, e.g., by make or model. Probe 100 can also be identified by a unique identifier that is associated with a single individual probe 100. The probe identifier can include a serial number or code that is subsequently associated with data collected by probe 100 to identify that this data was collected by probe 100. In some embodiments, each individual electrode, or a patch or strap containing a set of electrodes incorporates an integrated circuit memory having a stored unique or quasi-unique electrode/patch identifier. An interface between the patch or electrodes and the communication device 505 can be implemented so that the communication device 505 can send electrode or patch identifiers as well as a separate identifier for the other electronics coupled to the patch. In this way, different parts of the probe can be separately replaced, while still allowing complete tracking of the physical data generation, analysis, and communication apparatus used to gather all impedance data.

The data communicated along wireless data link 1125 can also include messages to probe 100. Example messages include commands to change measurement and/or data analysis parameters and queries regarding the status and/or operational capabilities of the probe. Data communication along wireless data link 1125 can also include information related to the initialization and activation of probe 100. Initialization can include the communication of a probe identifier to data collection apparatus 1105. Initialization can also include the commencement of measurement activities including, e.g. the start of an internal clock that regulates the timing of hydration measurements and the transmission of hydration measurement results. Such data communication can be conducted as an ongoing dialogue with data collection apparatus 1105.

Figure 12:
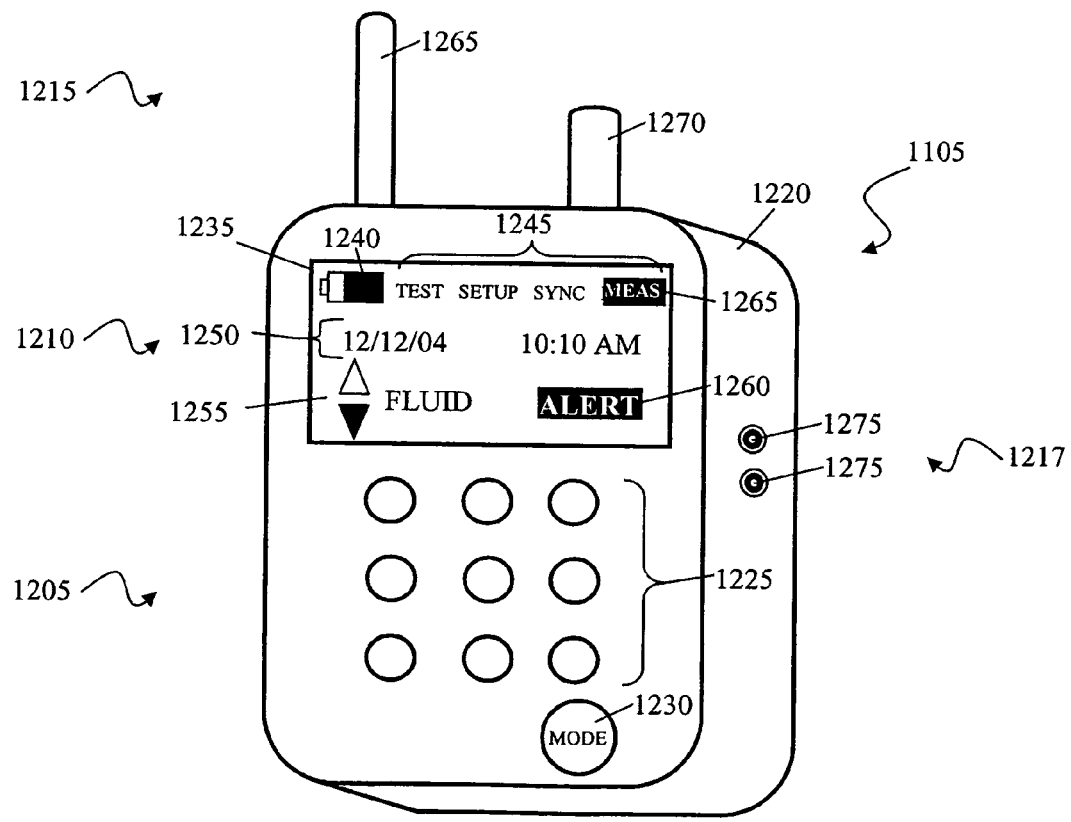
FIG. 12 shows a data collection apparatus that is usable in a system for monitoring the hydration of an organism.

Data collection apparatus 1105 is a device that generally supplements probe 100 by including components and/or features that complement the components and/or features of probe 100. For example, such components or features may be too large, too memory intensive, require too sophisticated data processing, and/or only be used too intermittently to be included on probe 100. FIG. 12 shows one implementation of a data collection apparatus 1105. Data collection apparatus 1105 can be a portable device in that data collection apparatus 1105 can be moved from a fixed location and perform at least some functions without input from a fixed device. For example, data collection apparatus 1105 can be a handheld device that can be borne by a monitored individual.

Data collection apparatus 1105 includes a local user input portion 1205, a local user output portion 1210, a wireless data communication portion 1215, and a wired data communication portion 1217 all arranged on a body 1220. Local user input portion 1205 includes one or more components that receive visual, audio, and/or mechanical input from a user in the vicinity of data collection apparatus 1105. For example, local user input portion 1205 can include a keypad 1225 and a mode selection button 1230. Keypad 1225 can receive alphanumeric input from a user. Mode selection button 1230 can receive an operational mode selection from a user. The operational modes of data collection apparatus 1105 are discussed further below.

Local user output portion 1210 includes one or more components that provide visual, audio, and/or mechanical output to a user in the vicinity of data collection apparatus 1105. For example, local user output portion 1210 can include a display panel 1235. Display panel 1235 can be, e.g., a liquid crystal display screen. Display panel 1235 includes various regions that display specific information to a local user. In particular, display panel 1235 includes a battery charge display region 1240, an operational mode display region 1245, a time/date display region 1250, a measurement result display region 1255, and an alert display region 1260.

Battery charge display region 1240 includes a graphical device that indicates the charge remaining on a battery or other power element that powers data collection apparatus 1105. Operational mode display region 1245 includes a text list of the various operational modes of data collection apparatus 1105. The listed operational modes include a test mode, a set-up mode, a synchronization mode, and a measurement mode. The text indicating measurement mode (i.e., "MEAS") includes an indicium 1265 that indicates that the current operational mode of data collection apparatus 110S is the measurement mode. Time/date display region 1250 includes text indicating the current time and date. Measurement result display region 1255 includes text and/or graphical elements that indicate the result(s) of a hydration measurement made by one or more probes 100. Alert display region 1260 includes a text and/or graphical warning that the probe measurement results are indicative of one or more disease states being present or imminent. Alert display region 1260 can also indicate that a malfunction of probe 100 and/or data collection apparatus 1105 is occurring or imminent.

Wireless data communication portion 1215 can include a first wireless communication transceiver 1265 and a second wireless communication transceiver 1270. Transceivers 1265, 1270 can be separate devices or transceivers 1265, 1270 can include common components for the wireless communication of data. For example, transceivers 1265, 1270 can each include a separate RF antenna.

Transceivers 1265, 1270 can be dedicated to the exchange of data with a particular device, or a particular class of devices. For example, transceiver 1265 can be dedicated to the exchange of data with one or more probes 100 over one or more wireless data links 1125, whereas transceiver 1270 can be capable of exchanging data with other data collection apparatus and/or with one or more data management systems 1110. Transceivers 1265, 1270 can function with cellular communication networks, alpha-numeric paging networks, WiFi or other systems for the wireless exchange of data.

Wired data communication portion 1217 can include one or more connector ports 1274 adapted to receive a plug or other terminal on one or more wired data links. The wired data links can be capable of exchanging data with other data collection apparatus and/or with one or more data management systems 1110. The wired data link can be an optical data link and/or an electrical data link. Electrical data links can be analog or digital. The data links can operate in accordance with data communication protocols such as the TCP/IP suite of communications protocols.

Body 1220 can be sealed to isolate electrical and other components (not shown) that perform operations such as driving portions 1205, 1210, 1215, 1217 from the ambient environment. Body 1220 can be sized and the components selected to allow data collection apparatus 1105 to be self-powered by an internal power supply (not shown). For example, data collection apparatus 1105 can be powered by an internal rechargeable battery. The components can be, e.g., data storage devices, data processing devices, data communication devices, and driving circuitry for managing the input and output of data from data collection apparatus 1105.

Body 1220 can be designed to operate as an independent unit as shown or body 1220 can be designed to integrate with separate communication devices. For example, body 1220 can be designed to integrate with a cellular phone or personal data assistant to form all or a portion of wireless data communication portion 1215.

Returning to FIG. 11, system 1100 can include a wired data link 1130 and/or a wireless data link 1135 for the exchange of data between data collection apparatus 1105 and data management system 1110. Wired data link 1130 can terminate at a connector port 1274 on data collection apparatus 1105, and wireless data link 1135 can terminate at transceiver 1270 on data collection apparatus 1105.

Wireless data link 1125, wired data link 1130 and wireless data link 1135 can exchange data in accordance with one or more communication protocols. The communication protocols can determine the format of the transmitted information and the physical characteristics of the transmission. Communication protocols can also determine data transfer mechanisms such as synchronization mechanisms, handshake mechanisms, and repetition rates. The data structures of the protocol may impact the rate of data transfer using the protocol. Data can be organized in blocks or packets and transmissions can be made at specified intervals. For example, a transmission block can include synchronization bits, an address field that includes information identifying the data source, a data field containing the hydration monitoring data, and a checksum field for testing data integrity at the receiver. The length of a data block can vary, e.g., to reduce power consumption and increase device lifetime. The same data can be transmitted multiple times to ensure reception.

In one implementation, exchanged data is organized in packets that include four sections, namely, a header section, a 64 bit address section that includes a probe identifier identifying a probe 100 (and/or an electrode or electrode set identifier), an encrypted data section, and a check-sum or error correction section. The data section can be encrypted using an algorithm that relies upon the address section.

Probe 100, data collection apparatus 1105, and data management system 1110 can all confirm a successful exchange of data using a confirmation such as an electronic handshake. An unsuccessful exchange of data can be denoted by transmission of an error message, which can be responded to by a retransmission of the unsuccessfully exchanged data.

In some implementations, probe 100, data collection apparatus 1105, and data management system 1110 can exchange data at a number of different frequencies. For example, when system 1100 includes multiple data collection apparatus 1105, each data collection apparatus 1105 can transmit data over wireless data link 1135 using a different frequency carrier. As another example, when system 1100 includes multiple probes 100, each probe 100 can transmit data over wireless data link 1125 using a different frequency carrier. It will be appreciated that a variety of multiple access techniques such as time or code division, could be alternatively used.

The data communicated along wireless data link 1125, wired data link 1130, and wireless data link 1135 can be encrypted in whole or in part. The encryption can be symmetric or asymmetric. The encryption can rely upon encryption keys based on the probe identifier or on alphanumeric codes transmitted with the encrypted data. The encryption may be intended to be decrypted by a specific probe 100, a specific data collection apparatus 1105, or a specific data management system 1110. In one implementation, data communicated along wired data link 1130 is encrypted using 128 bit encryption at the SSL layer of the TCP/IP protocol.

Both proprietary and public protocols can be used to exchange data between probe 100, data collection apparatus 1105, and data management system 1110. For example, the global system for mobile communications (GSM), Bluetooth, and/or the internet protocol (IP) can be used.

In one implementation, wireless link 1125 is a spread-spectrum RF signal at wireless medical band frequencies such as the Medical Implant Communications Service (MICS) (400-406 MHz) or the Wireless Medical Telemetry Service (WMTS) (609-613 MHz and 1390-1395 MHz).

Data management system 1110 is a data processing device that conducts operations with the data collected by probe 100 that relates to hydration of the organism. The operations can be conducted in accordance with the logic of instructions stored in machine-readable format. The conducted operations can include the processing of such data, the display of such data, and the storage of such data.

Data management system 1110 can be remote from data collection apparatus 1105 in that data management system 1110 need not be part of a local data communication network that includes data collection apparatus 1105. For example, data management system 1110 can be a data processing apparatus that is accessible by one or more medical personnel.

The processing of data by data management system 1110 can include data analysis to identify disease states in monitored organisms or problems with the monitoring. For example, data management system 1110 can perform impedance analysis using model equivalent circuits to determine hydration levels at different locations in a monitored organism.

The display of data by data management system 1110 can include the rendition of the results of hydration monitoring on one or more input/output devices 1115. Input/output device 1115 can include visual, auditory, and/or tactile display elements that can communicate information to a human user (such as medical personnel). For example, input/output device 1115 can include a monitor, a speaker, and/or a Braille output device. Input/output device 1115 can also include visual, auditory, and/or tactile input elements such as a keyboard, a mouse, a microphone, and/or a camera. Input/output device 1115 can thus render visual, auditory, and/or tactile results to a human user and then receive visual, auditory, and/or tactile input from the user.

The storage of data by data management system 1110 can include the storage of the results of hydration monitoring on one or more data storage devices 1120 that retain information in machine-readable format. Data storage devices 1120 can include volatile and/or nonvolatile memory. For example, data storage devices 1120 can be a RAM device, a ROM device, and/or a memory disk.

In operation, all or some of the constituent components of system 1100 can operate in one or more operational stages. For example, during a test stage, the constituent components of system 1100 can test themselves to determine that they are functional. For example, probe 100 and data collection apparatus 1105 can confirm that they are capable of exchanging data along link 1125, and data collection apparatus 1105 and data management system 1110 can confirm that they are capable of exchanging data along one or more of links 1130, 1135. As another example, probe 100 can confirm that inputs 120, 125 and outputs 130, 135 are properly positioned relative to a monitored organism. For example, when inputs 120, 125 and outputs 130, 135 are electrodes 245, 250, 255, 260, probe 100 can confirm that electrodes 245, 250, 255, 260 are in electrical contact with the followed portion of the monitored organism.

During a setup stage, parameters relating to the monitoring of the hydration of an individual can be arranged. For example, a probe 100 can determine the baseline measurement result for a given hydration level in a portion of a monitored organism and adjust monitoring parameters accordingly. For example, the input signal level can be increased to accommodate dry skin and high transdermal impedances. Data collection apparatus 1105 can receive user input over one or more of local user input portion 1205, wireless data communication portion 1215, and wired data communication portion 1217. The received input can identify monitoring parameters that are to be adjusted, such as the level at which an alert is to be sounded at probe 100 and/or data collection apparatus 1105. Data management system 1110 can also receive user input relating to the arrangement of monitoring parameters. For example, data management system 1110 can receive input from medical personnel over input/output device 1115 indicating that hydration measurement results are to be transmitted by probe 100 to data collection apparatus over link 1125 once every four hours. This timing parameter can be relayed from data management system 1110 over link 1130 to data collection apparatus 1105 which relays the timing parameter over wireless link 1125 to probe 100.

Parameters relating to the communication of information over one or more of links 1125, 1130, 1135 can also be arranged during a setup stage. For example, the constituent components of system 1100 can select communication protocols or parameters for communication protocols.

During a synchronization stage, clocks in two or more of probe 100, data collection apparatus 1105, and data management system 1110 are synchronized to enable synchronous data transmission along one or more of links 1125, 1130, 1135. For example, in one implementation, data collection apparatus 1105 transmits synchronization characters to data management system 1110 over wired data link 1130. Data management system 1110 can receive the synchronization characters and compares the received characters with a synchronization pattern. When the received characters correspond sufficiently with the synchronization pattern, data management system 1110 can exit the synchronization stage and exchange other data synchronously with data collection apparatus 1105 over link 1130. Such a synchronization process can be repeated periodically.

In one implementation, data collection apparatus 1105 can receive and/or display a serial number or other identifier of a synchronized probe 100.

During a measurement stage, one or more probes 100 can collect data relating to the hydration of one or more monitored individuals. The probes 100 can perform data processing on the collected data, including bioelectric impedance data analysis, filtering, and, event identification.

The probes 100 can transmit data relating to the hydration monitoring (including results of processing and analyzing collected data) to one or more data collection apparatus 1105. The transmitted data can include a probe identifier that identifies the transmitting probe 100. The transmitted data can be encrypted.

Data collection apparatus 1105 can receive the data transmitted from probe 100 and update local user output portion 1210 based on the received data. The updating can include indicating, in operational mode display region 1245, that probe 100 is monitoring hydration, displaying, in measurement result display region 1255, recent monitoring results, and generating, in alert display region 1260, an alert to a user who is local to data collection apparatus 1105. The alert can indicate, e.g., that a monitored individual is suffering from one or more disease states or that monitoring has somehow become impaired.

Data collection apparatus 1105 can also command one or more probes 100 to transmit data relating to the hydration monitoring over link 1125. For example, data collection apparatus 1105 can transmit a query to probe 100. The query can request that probe 100 provide information regarding some aspect of the hydration monitoring. For example, a query can request that probe 100 transmit a confirmation that hydration monitoring is occurring over link 1125, a query can request that probe 100 transmit a recent measurement result over link 1125, or a query can request that probe 100 transmit one or more events of a particular character over link 1125. Data collection apparatus 1105 can transmit queries to probe 100 periodically, e.g., every hour or two.

Data collection apparatus 1105 can also relay some or all of the data transmitted from probe 100 to data management system 1110. The data can be relayed over one or more data links 1130, 1135. Data collection apparatus 1105 can relay such data directly, i.e., without performing additional analysis on the information, or data collection apparatus 1105 can perform additional processing on such before relaying a subset of the data to data management system 1110. Data collection apparatus 1105 can notify a local user that data has been relayed by displaying a data relay notice on local user output portion 1210. Alternatively, data can be relayed by data collection apparatus 1105 without notification to a local user.

Data collection apparatus 1105 can also receive user input over one or more of local user input portion 1205, wireless data communication portion 1215, and wired data communication portion 1217. The received input can identify that data collection apparatus 1105 is to transmit data to one or more probes 100 over link 1125. For example, the received input can identify that data collection apparatus 1105 is to instruct probe 100 to generate an alarm signal indicating that a monitored person suffers under a disease state. As another example, the received input can identify that data collection apparatus 1105 is to transmit a query to a probe 100 over wireless link 1125. As another example, the received input can identify that data collection apparatus 1105 is to transmit an instruction instructing probe 100 to change a parameter of the hydration monitoring, including one or more threshold values for identifying a disease state.

Data collection apparatus 1105 can also perform data processing and storage activities that supplement the data processing and storage activities of probe 100. For example, data collection apparatus 1105 can perform more extended data analysis and storage, including signal processing and analysis. For example, data collection apparatus 1105 can perform impedance analysis using model equivalent circuits to determine hydration levels at different locations in a monitored organism. As another example, data collection apparatus 1105 can perform trending analyses that identify a general tendency of hydration levels to change over extended periods of time, or data collection apparatus 1105 can perform comparisons between hydration levels obtained using multiple probes 100. The multiple probes 100 can monitor the hydration of a single organism, or the multiple probes can monitor the hydration of multiple organisms. Data collection apparatus 1105 can compare and correlate monitoring results from multiple probes to calibrate one or more probe 100 and minimize errors during monitoring.

Data collection apparatus 1105 can also compare and/or correlate the results of hydration monitoring with the results of monitoring other biological parameters. For example, data collection apparatus 1105 can compare and correlate the results of hydration monitoring with the results of heart monitoring, drug delivery schedules, and temperature monitoring. Data collection apparatus 1105 can receive the other monitoring results over one or more of local user input portion 1205, wireless data communication portion 1215, and wired data communication portion 1217. For example, data collection apparatus 1105 can receive the other monitoring results over one or more of links 1125, 1130, 1135.

Data collection apparatus 1105 can also exchange data with other devices and systems (not shown in FIG. 11). For example, data collection apparatus 1105 can receive other monitoring results directly from other monitoring instruments. As another example, data collection apparatus 1105 can transmit data relating to the results of hydration monitoring to other local or remote parties. The other parties can be external entities in that they do not share a legal interest in any of the constituent components of system 1100. For example, the other parties can be a medical group that has contracted with an owner of system 1100 to monitor hydration of an individual.

Data management system 1110 can receive the results of hydration monitoring from data collection apparatus 1105 over one or both of data link 1130, 1135. The received results can include analyses of the hydration of an organism, as well as comparisons and correlations of monitoring results from multiple organisms or other biological parameters.

Data management system 1110 can conduct operations with the received data, including processing the data to identify disease states and problems with the monitoring. For example, data management system 1110 can perform impedance analysis using model equivalent circuits to determine hydration levels at different locations in a monitored organism. As another example, data management system 1110 can perform trending analyses that identifies a general tendency of hydration levels to change over extended periods of time, or data management system 1110 can perform comparisons between hydration levels obtained using multiple probes 100. The multiple probes 100 can monitor the hydration of a single organism, or the multiple probes can monitor the hydration of multiple organisms. Data management system 1110 can compare and correlate monitoring results from multiple probes to calibrate one or more probe 100 and minimize errors during monitoring. Data management system 1110 can also perform analyses that require hydration monitoring results from statistically significant numbers of organisms. Such analyses can include billing assessments, geographic assessments, epidemiological assessments, etiological assessments, and demographic assessments.

Data management system 1110 can render the results of hydration monitoring on one or more input/output devices 1115 and store the results of hydration monitoring on one or more data storage devices 1120. Data management system 1110 can also provide the results of the data processing to data collection apparatus 1105 and/or probe 100 over data links 1125, 1130, 1135. The provided results can include an indication that a disease state is present and/or an indication that probe 100 should generate an alarm signal indicating that a monitored organism suffers under a disease state. Data management system 1110 can also provide such indications to external entities, including medical personnel interacting with input/output device 1115 and medical personnel in the vicinity of the monitored organism. For example, an emergency medical technician (EMT) can be informed that a monitored individual in the EMT's vicinity suffers from acute dehydration. As another example, data management system 1110 can also post an indication in an external system such as the clinical information system of a healthcare organization or an Internet portal.

In one implementation, data management system 110 can request, from data collection apparatus 1105 and/or probe 100, that additional monitoring activities be performed. The request can be spurred by the results of analyses performed at data collection apparatus 1105 and/or the analyses performed at data management system 1110. The request can also be spurred by a human user such as medical personnel interacting with input/output device 1115. The requests can be based on the results of hydration monitoring. The additional monitoring activities can be directed to other biological parameters, or the additional monitoring activities can be directed to gaining more information about the hydration of the monitored individual. For example, data management system 1110 can identify surveys and/or survey questions that are to be presented to a monitored organism to facilitate hydration monitoring. A survey is a series of questions designed to gather information about the hydration of a monitored organism. A survey is generally presented to a monitored organism, but a survey can also be presented to individuals having contact with the monitored organism. A survey can be presented, e.g., over a telephone or through the mail. Survey and survey questions can be generated before monitoring begins and stored, e.g., at probe 100, data collection apparatus 1105, and/or data management system 1110.

Survey questions can be directed to ascertaining, e.g., body position of a monitored organism, length of time that the monitored organism has been in one position, the diet of the monitored organism, the activity level of the monitored organism, or the time zone of the monitored organism. Example survey questions include "Are you currently exercising?", "Did you remove the probe?", and "Have you recently taken a diuretic?" The questions presented during a survey can depend upon the responses to previous questions. For example, if a monitored individual has removed probe 100, subsequent questions can be deleted.

Responses to the questions in the survey can be received using, e.g., an interactive voice recognition system (IVRS) or keypad entry on a touch tone phone. Data management system 1110 can present the survey itself or data management system 1110 can direct another system to present the survey. The responses to survey questions can be scored based upon a predetermined criteria set and used in further analyses in hydration monitoring.

Figure 13:
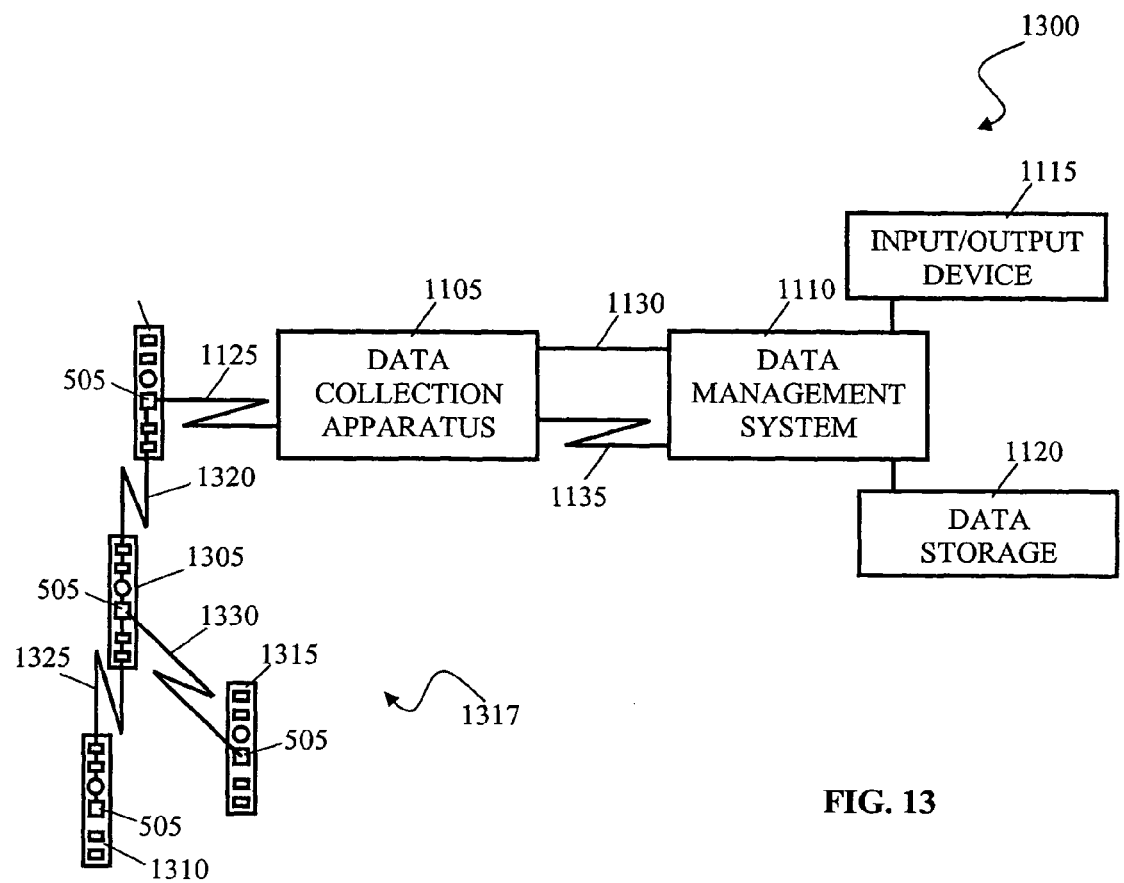
FIG. 13 shows another system for monitoring the hydration of an organism.

FIG. 13 shows another implementation of a system for monitoring the hydration of an organism, namely a system 1300. In addition to one or more data collection apparatus 1105, data management system 1110, input/output device 1115, and data storage device 1120, system 1300 includes a collection of multiple probes 100, 1305, 1310, 1315. Together, probes 100, 1305, 1310, 1315 form a data "hopping" network 1317 in which data can be transferred amongst probes 100, 1305, 1310, 1315. In particular, in network 1317, probe 1305 exchanges data with probe 100 over a wireless data link 1320. Probe 1310 exchanges data with probe 1305 over a wireless data link 1325. Probe 1315 exchanges data with probe 1310 over a wireless data link 1330. The data exchanged amongst probes 100, 1305, 1310, 1315 over data links 1320, 1325, 1330 can include hydration monitoring results, biological parameter monitoring results, queries, parameter change commands, encryption keys, probe identifiers, handshakes, surveys, and other information.

Such a "hopping" network 1317 may extend the range and robustness of data communication in system 1300.

Figure 14:
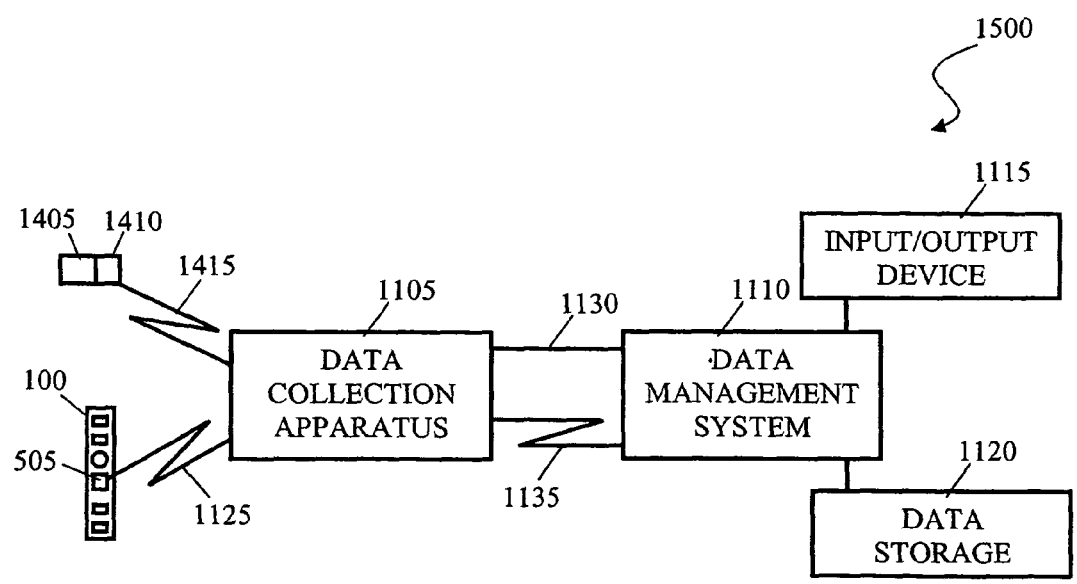
FIG. 14 shows another system for monitoring the hydration of an organism.

FIG. 14 shows another implementation of a system for monitoring the hydration of an organism, namely a system 1400. In addition to one or more data collection apparatus 1105, data management system 1110, input/output device 1115, and data storage device 1120, system 1400 includes a pharmaceutical dispenser 1405. Pharmaceutical dispenser 1405 is a device that provides compositions for ameliorating a disease state of an individual. Pharmaceutical dispenser 1405 can provide such a composition to an individual automatically (i.e., without human intervention) or pharmaceutical dispenser 1405 can provide such a composition in conjunction with the efforts of one or more individuals. For example, pharmaceutical dispenser 1405 can be an implanted controlled-release drug delivery device or pharmaceutical dispenser 1405 can be a pill dispenser that is accessible by a monitored individual or by medical personnel.

Pharmaceutical dispenser 1405 includes a communications element 1410. Communications element 1410 can place dispenser 1405 in data communication with the constitutent components of system 1400. For example, in one implementation, communications element 1410 can establish a wireless data link 1415 between dispenser 1405 and data collection apparatus 1105.

In operation, pharmaceutical dispenser 1405 can receive data such as dispensation instructions from the constituent components over communications element 1410. For example, when one or more of probe 100, data collection apparatus 1105, and data management system 1110 identify, based at least in part on the results of hydration monitoring, that a monitored individual suffers under one or more disease states, pharmaceutical dispenser 1405 can receive instructions over element 1410 that instruct dispenser 1405 to provide a composition to the monitored individual that ameliorates the identified disease state.

In response to the receipt of dispensation instructions, pharmaceutical dispenser 1405 can provide a composition for ameliorating a disease state to the monitored individual. For example, pharmaceutical dispenser 1405 can release a drug into the monitored individual's body or pharmaceutical dispenser 1405 can prepare a dosage of medicine for the monitored individual. The dispensation of a composition by pharmaceutical dispenser 1405 can be recorded at one or more memory devices in system 1400, e.g., for use in analyzing the results of hydration monitoring.

Figure 15:
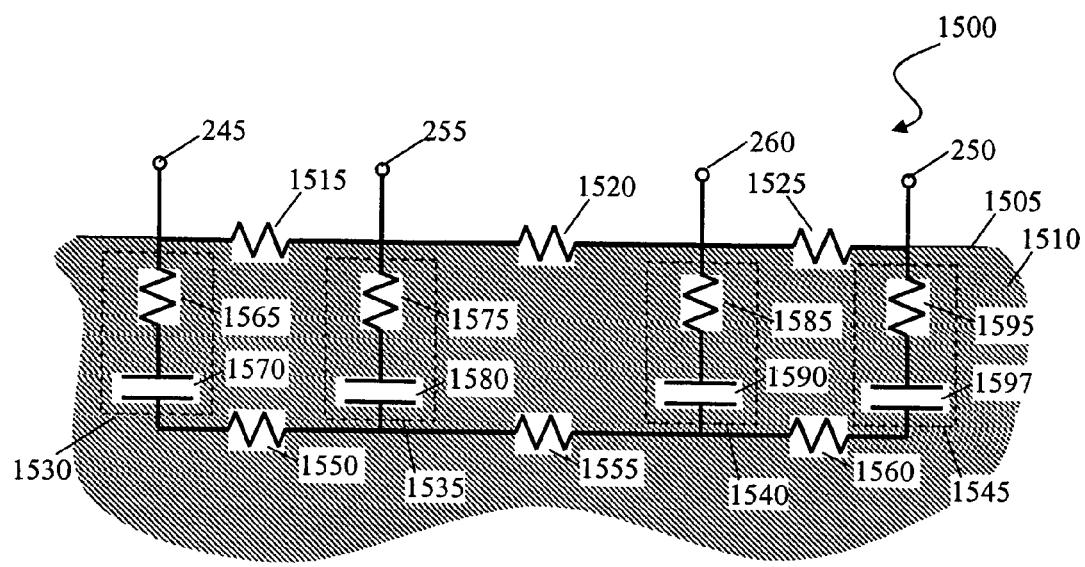
FIG. 15 shows an example of a model equivalent circuit that can be used in monitoring the hydration of an organism.

FIG. 15 shows an example of a model equivalent circuit 1500 that can be used in monitoring the hydration of an organism. In particular, model equivalent circuit 1500 that can be used to model the electrical conductivity of an organism. Circuit 1500 models the impedances observed in bioelectric impedance spectroscopy using a probe 200 that supports electrodes 245, 250, 255, 260 above a skin surface 1505 of an organism 1510.

Model circuit 1500 includes a series of surface impedances 1515, 1520, 1525, a series of transdermal impedances 1530, 1535, 1540, 1545, and a series of subdermal impedances 1550, 1555, 1560. Surface impedances 1515, 1520, 1525 can model the surface electrical impedances between the relevant of electrodes 245, 250, 255, 260. Surface impedances 1515, 1520, 1525 can model both the conductivity through the surface of the skin and the conductivity through sweat and other conducting fluids on the surface of the skin. In one implementation, surface impedances 1515, 1520, 1525 are modeled as non-reactive (i.e., resistive) elements.

Transdermal impedances 1530, 1535, 1540, 1545 can model the electrical impedances through the skin of a monitored organism. Transdermal impedance 1530 includes a resistive component 1565 and a reactive component 1570. Transdermal impedance 1535 includes a resistive component 1575 and a reactive component 1580. Transdermal impedance 1540 includes a resistive component 1585 and a reactive component 1590. Transdermal impedance 1545 includes a resistive component 1595 and a reactive component 1597. Reactive components 1570, 1580, 1590, 1597 can model the electrical impedance through dense cellular layers as a capacitive element, whereas resistive components 1565,

1575, 1585, 1595 can model the electrical impedance through hydrated and other portions of the skin as a resistive element.

Subdermal impedances 1550, 1555, 1560 can model electrical impedances through a monitored organism. For example, subdermal impedances 1550, 1555, 1560 can model the electrical impedances of a portion of the monitored organism as a resistive volume conductor bounded by the skin.

In one implementation, in bioelectric impedance spectroscopy, probe 200 supports electrodes 245, 250, 255, 260 above skin surface 1505. Current source 210 can drive electrical current between electrodes 245, 250. The driven current can include both direct current and alternating current components. The potential at electrodes 245, 250, 255, 260 provides information about the net impedance across equivalent circuit 1500 as well as the impedance of different paths across equivalent circuit 1500.

For example, when direct current is driven across circuit 1500, a large portion of the direct current will pass through surface impedances 1515, 1520, 1525. Potential measurements at electrodes 245, 250, 255, 260 under direct current application can be used to estimate the impedance of surface impedances 1515, 1520, 1525. When certain frequencies of alternating current are driven through circuit 1500, some portion of the alternating current can pass through surface impedances 1515, 1520, 1525, transdermal impedances 1530, 1535, 1540, 1545, and subdermal impedances 1550, 1555, 1560. Potential measurements at electrodes 245, 250, 255, 260 can be used to estimate impedances 1515, 1520, 1525, 1530, 1535, 1540, 1545, 1550, 1555, 1560. Such estimations can be made in light of the estimations of surface impedances 1515, 1520, 1525 made using direct current.

The impact of various factors on the electrical conductivity of an organism can be accommodated by changing the mathematical analysis of model circuit 1500 or by changing aspects of data collection. For example, when surface impedances 1515, 1520, 1525 are particularly low, e.g., due to heightened conductivity through sweat or other conducting fluids on the surface of the skin, the measured potentials at electrodes 245, 250, 255, 260 can be mathematically corrected to accommodate the lowered conductivity. For example, previously obtained surface impedance estimates can be used to estimate the effect that changes in surface impedances 1515, 1520, and 1525 have on the total impedance measurement, and thus isolate the change in sub-dermal impedance so as to more accurately monitor changes in subdermal tissue hydration. Alternatively, bioelectric spectroscopy measurements can be delayed altogether or probe 200 can output an indication to a monitored individual that the individual should dry the measurement region.

Model equivalent circuit 1500 can be used in conjunction with custom approaches to data analysis for monitoring the hydration of an organism. Such data analysis approaches can be used to interpret monitoring data and to identify changes in the amount and distribution of water in a monitored organism. Data analysis approaches can also be used to incorporate results of other bioparameter measurements and responses to survey questions into the hydration monitoring.

Data analysis approaches can be performed in accordance with the logic of a set of machine-readable instructions. The instructions can be tangibly embodied in machine-readable format on an information carrier, such as a data storage disk or other memory device. The instructions can also be embodied in whole or in part in hardware such as microelectronic circuitry.

Data analysis approaches can yield analysis results that can be displayed to a human user. The human user can be the monitored individual or another individual, such as a medical professional. The analysis results can be displayed in response to a prompt from the user or automatically, i.e., without user input. For example, the analysis results can be displayed automatically when hydration indicative of a disease state is identified. When hydration monitoring is performed using a system 1100, analysis results can be displayed at a probe 100, at a data collection apparatus 1105, and/or at a data management system 1110 (FIGS. 11, 13, 14). Analysis results can be displayed using other output devices such as the postal service, facsimile transmission, voice messages over a wired or wireless telephone network, and/or the Internet or other network-based communication modalities.

Data analysis can be performed continuously or intermittently over extended periods of time. The analyzed data can be measurement results collected continuously or intermittently. The analyzed data can be a subset of the data collected or the analyzed data can be all of the data collected. For example, the analyzed data can be intermittent samples redacted from the results of continuous hydration monitoring.

One advantage of the analysis of hydration monitoring results obtained over extended periods of time is that long term monitoring may be achieved. The monitoring can be long term in that diurnal, monthly, or other variations in hydration that are not associated with disease states can be identified. The monitoring can be individualized in that the analysis results are relevant to a specific monitored organism.

Data analysis can accommodate both long and short term variations in hydration that are not associated with disease states by reducing the effect of such variation on analysis. For example, data analysis can accommodate variations associated with respiration and other types of movement. For example, peak/trough analysis and/or frequency analysis of hydration monitoring results obtained from the chest can be used to determine the breathing period. This can be done, e.g., by identifying the rate of change between discrete data points in the measurement results. Once the breathing period is identified, specific measurement results (such as those associated with exhalation) can be identified and relied upon in subsequent analyses.

Changes in impedance measurements due to electrode movement over time or with wear can also be accommodated in data processing routines if necessary.

As another example, data analysis can accommodate diurnal or monthly variations. Such variations can be identified by peak/trough analysis and/or frequency analysis of longer term measurement results. For example, specific measurement results (such as those associated with exhalation) can be used to identify any reproducible diurnal and/or monthly variability in hydration. Such variability can be accommodated in subsequent measurement results by subtraction of the prior variability or other adjustment approaches.

For example, the diurnal pattern of hydration monitoring results may indicate that there is a significant likelihood of a 3% decrease in a bioelectric impedance value for a specific organism in the late afternoon relative to early morning. Hydration measurement results obtained at either time may be adjusted or modified by interpolation to reflect the decrease. Such adjustments can be made to account for predictable or habitual patterns such as, e.g., daily exercise routines or eating/drinking habits.

As another example of accommodating diurnal variations, only measurement results obtained during patterned times of regular breathing (for example, during sleep) are relied upon in subsequent analyses. Such patterned times can be identified, for example, by determining the rate of change in hydration monitoring results. Such patterned times can be used in conjunction with measurement results obtained with a known hydration status (e.g., the monitored individual is "dry" and unaffected by pulmonary edema) to adjust decision criteria and other analysis parameters.

Other variations in hydration monitoring results, including random variations such as electronic stray signal or positional signal noise, can be accommodated using digital and/or analog filters, signal averaging, data discarding techniques, and other approaches.

Data analysis of hydration monitoring results can be used to establish a baseline of typical hydration characteristics so that deviations from the baseline, e.g., in response to disease states or other stresses, can be identified. The baseline of typical hydration characteristics can be individualized and relevant to a specific monitored organism, or the baseline of typical hydration can reflect the average hydration of a population of individuals. For example, extended monitoring results can be analyzed to establish a population database of tolerances and ranges for the identification of individual disease states, deviations, and/or anomalies, as well as population trends (as discussed further below). Such a baseline can be obtained for healthy and/or diseased populations with a variety of demographic characteristics.

In contrast, transient periodic hydration monitoring of an individual (such as, e.g., monitoring an individual for a short time once a day or once a week) is less likely to detect individual variations, deviations, or anomalies and does not contribute to the establishment of a population database.

Data analysis can include the analysis of subsets of the total hydration monitoring results. The analyzed subsets can have common characteristics that distinguish the subsets from unanalyzed hydration monitoring results. For example, the analyzed subsets can have high signal-to-noise ratios, analyzed subsets can be obtained under dry conditions (e.g., when surface impedances 1515, 1520, 1525 (FIG. 15) are relatively high), analyzed subsets can be obtained when good contact is maintained between a monitored organism and inputs 120, 125 and outputs 130, 135 (FIG. 1), or analyzed subsets can be obtained at the same time of day.

Data analysis operations can be performed at one or more of probe 100, data collection apparatus 1105, and/or data management system 1110. In one implementation, data analysis is distributed between probe 100 and data collection apparatus 1105. In particular, probe 100 can perform initial analyses, including signal processing, noise filtering, and data averaging operations. The operations can be performed on data from one or more measurements taken at one or more frequencies. The operations can be performed on raw data or on data where variations have been accommodated. For example, the operations can be performed on data collected at certain points during breathing. These initial analysis results can be transmitted, along with other information such as a probe identifier and a time/date stamp, to data collection apparatus 1105. At data collection apparatus 1105, data analysis operations can include the identification of trends or shifts in hydration associated with disease states such as pulmonary edema, as well as comparisons between received data and threshold values.

In another implementation, data analysis operations are performed primarily at data collection apparatus 1105 and data analysis at probe 100 is minimal. When data analysis at probe 100 is minimal, data analysis and data storage can be consolidated at data collection apparatus 1105 and probe 100 can include simplified circuitry with reduced power requirements and cost.

Data analysis can also be performed at data management system 1110. Such data analysis can include multivariable analysis where hydration monitoring results are analyzed in light of other statistical variables such as weight, heart rate, respiration, time of day, month, eating patterns, physical activity levels, and other variables. The other statistical variables need not be entirely independent of the hydration monitoring results. The hydration monitoring results used in multivariable analysis can be obtained over extended periods (e.g., days, weeks, or months) from one or more organisms. The results of such multivariable analysis can be used to develop new and improved analyses of hydration monitoring results, including improved algorithms, improved pattern definition techniques, and/or artificial intelligence systems.

A variety of other analysis techniques can be applied to hydration monitoring results. These include the use of established guideline values for data that is used to determine fluid changes associated with the onset or progression of pulmonary edema. Also, clinician-modified variables such as tailored threshold values can be applied to permit increased accuracy and specificity.

These and other analyses of hydration monitoring results can be made in light the results of monitoring other biological parameters such as respiration, heart rate, hormone (e.g., B-type natriuretic peptide (BNP)) levels, metabolite levels (e.g., blood urea nitrogen (BUN) and/or $Na^+/K^+$ levels), wedge pressure measurements, electrocardiogram measurements, and others. Analyses made in light of such other parameters may improve the information provided by the analysis process.

Data analysis can include comparisons involving recent hydration monitoring results. For example, recent hydration monitoring results can be compared with previous hydration monitoring results, predicted results, or population results. Future hydration monitoring results can be predicted based on the current state of the monitored individual and on past hydration monitoring results obtained with the same or with other individuals or a population or demographic group. Such comparisons may include, for example, the use of population data tables, multiple reference measurements taken over time, or the results of trend analyses based upon extended hydration monitoring.

Such comparisons can also involve other factors, including other bioparameters. For example, hydration monitoring results can be weighted by one or more factors before comparisons are performed. Examples of such factors include the monitored individual's age, weight, height, gender, general fitness level, ethnicity, heart rate, respiration rate, urine specific gravity value, blood osmolality measurement, time of day, altitude, state of hydration (either subjective or objective), cardiac waveforms, left ventricle ejection fraction, blood oxygen levels, secreted potassium or sodium ions levels, skin surface temperature, ambient temperature, core body temperature, activity/motion assessment, humidity, and other bioparameters.

With trend analysis and prediction of future hydration state, it is possible to prevent serious hydration problems from occurring by providing treatment or intervention recommendations to the subject and/or a care provider prior to serious hydration problems occurring. For ambulatory healthy subjects, a downward hydration trend over a selected period can be detected and a recommended fluid intake could be presented automatically. The timing and nature of the recommendation could be also based at least in part on the age, gender, or other relevant factors. For some conditions, such as a prediction that fluid is building in lung tissue during the onset of pulmonary edema, a recommended intake of a pharmaceutical agent can be automatically provided.

Hydration monitoring can proceed in a variety of different environments using a variety of different procedures to monitor a variety of different disease states. For example, in one implementation, where hydration is monitored for indications of pulmonary edema, monitoring can commence after an individual has been identified as at risk for pulmonary edema. For example, such an individual may have been admitted to a care facility for treatment of pulmonary edema. Hydration can be monitored as the individual is "dried out" and excess fluid load in the thoracic region is reduced. Hydration monitoring can be continued after the individual is "dried out." For example, hydration monitoring can continue after such an individual is released from the care facility, and even as the individual returns to performing workday activities. Through all or a part of this time, hydration monitoring can be ongoing and rely upon a portable probe that can be moved from a fixed location by the individual and still perform at least some output signal generation. Analysis of the results of such hydration monitoring can be used to gather information about the reonset and/or progression of pulmonary edema, both in the monitored patient and in population groups that include the monitored patient.

Hydration monitoring can be performed to achieve a variety of different objectives, including the identification of levels and distributions of water in organisms that are indicative of one or more acute or chronic disease states. Examples of such monitoring follow.

EXAMPLE 1

Ambulatory Bioelectric Impedance Monitoring to Monitor Dehydration of an Individual Many individuals find themselves in activities or in environments that are conducive to dehydration. Such activities may include athletics, public safety activities performed by officers/firefighters, combat, and other activities requiring physical exertion. Such environments include hot and humid locales.

In these cases, one or more strap probes can be deployed along a thigh of such individuals to continually monitor the hydration of such individuals. Alternatively, probes can be incorporated into clothing such as the pants and sock illustrated in FIGS. 9A and 9B.

During the initialization of hydration monitoring, a range of data, including hydration monitoring results and the results of monitoring other bioparameters, can be transmitted to one or more data processing devices that perform analysis operations. The transmitted data can be used by such devices to establish a baseline from which relative changes in hydration can be determined. The transmitted data can include, e.g., urine specific gravity, blood osmolality, and/or other parameters indicative of hydration status, including, e.g., anthropometric data such as segment size, age, height, weight, and general fitness level.

The established baseline can be returned to the probe and used by the probe to provide instantaneous alarms when hydration monitoring results indicative of dehydration are obtained. Further, the results of hydration monitoring generated by the probe can be transmitted to a data collection apparatus and/or data management system for analysis and archiving.

A data collection apparatus and/or data management system can also identify hydration monitoring results that are indicative of dehydration. For example, when hydration decreases by a certain threshold amount (e.g., 3%), a data collection apparatus and/or data management system can record the decrease and then trigger an alarm signal at the probe and/or the data collection apparatus. For example, the extent of dehydration can be displayed along with a recommended fluid replacement volume and a recommended recovery time. Further, the alert can be relayed to a third party such as an athlete's coach, a supervisor, or medical personnel.

Following a period of monitoring, the monitored individual can remove and replace a probe. The new probe can synched to the data collection apparatus and provided with new baseline impedance measurements.

EXAMPLE 2

Ambulatory Bioelectric Impedance Monitoring of Individuals Using a Data Collection Apparatus Incorporated into Other Equipment A data collection apparatus can be incorporated into a device commonly used by individuals who find themselves in activities or in environments that are conducive to dehydration. For example, a data collection apparatus can be incorporated into safety equipment, the handlebars of a bicycle, a helmet, or gloves. When hydration monitoring results indicative of a disease state such as dehydration are obtained, the data collection apparatus can alert the individual and/or others in the individual's vicinity of the results. For example, a light on the outside of a football player's helmet can flash to alert teammates and coaches of the player's hydration monitoring results. These alerts can be graded with the severity of the hydration monitoring results so that the player and teammates have timely warning prior to passing critical hydration thresholds, such as greater than 5% dehydration.

EXAMPLE 3

Ambulatory Bioelectric Impedance Monitoring of Individuals in Motorized Vehicles Many individuals who operate motor vehicles are ambulatory but have their mobility restricted in that they are confined within the vehicle for extended times. Such vehicles include cars, airplanes, tanks, ships, and other transportation devices.

Probes for monitoring the hydration of such individuals can be incorporated into motor vehicles, e.g., at a steering wheel, joystick, or other surface that contacts operating individuals either continually or intermittently. Intermittent contact can be accommodated by limiting data analysis to data obtained during periods of good contact between the probe and the monitored organism.

Such vehicles can also include a data collection apparatus. In some implementations, the data collection apparatus can share generic components with the vehicle to perform various operations. Such components include vehicle display systems and data communication devices.

When hydration monitoring results indicative of a disease state such as dehydration are obtained, the data collection apparatus can alert the individual and/or others in the individual's vicinity of the results. For example, a pit crew can be notified that a driver is becoming dehydrated or a commanding officer can be notified that soldiers in his/her command are becoming dehydrated.

Although a number of implementations have been described, changes may be made. For example, bandage probes can be incorporated into clothing. Probe 100 can communicate with data collection apparatus 1105 by a wired data link. Both probe 100 and data collection apparatus 1105 can be incorporated into other items or equipment such as a vehicle, a radio unit, a shoe, football equipment, fire fighting equipment, gloves, hydration systems, bicycle handlebars, and other devices. Data communication along data link 1125 can be asynchronous, and the synch operational mode eliminated from data collection apparatus 1105.

Figure 16:
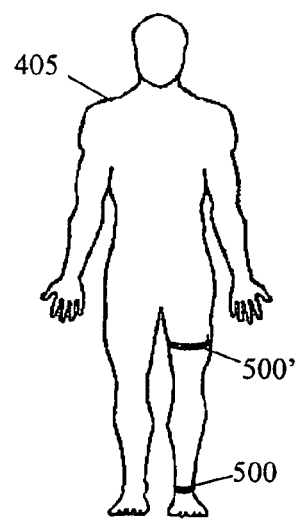
FIG. 16 illustrates an example deployment of multiple strap probes to monitor hydration.

As shown in FIG. 16, multiple probes (i.e., probes 500 and 500') can be deployed at different locations at an organism 405 to monitor the hydration of the organism. In particular, strap probe 500 is sized to encircle the thigh of person 405 and is deployed to probe the conductivity of the thigh of person 405, whereas strap probe 500' is sized to encircle the lower leg of person 405 and is deployed to probe the conductivity of the lower leg of person 405.

The measurement results from the probes 500, 500' can be compared and correlated for calibration and error minimization. For example, probe 500' can provide hydration measurement results that are used to identify disease states such as congestive heart failure where water accumulates in the lower legs, and probe 500 can provide hydration measurement results that are used to calibrate the hydration measurement results obtained using probe 500'. Such a calibration can include making differential measurements that accommodate variation in the hydration monitoring results that is unrelated to cardiac failure.

Figure 17:
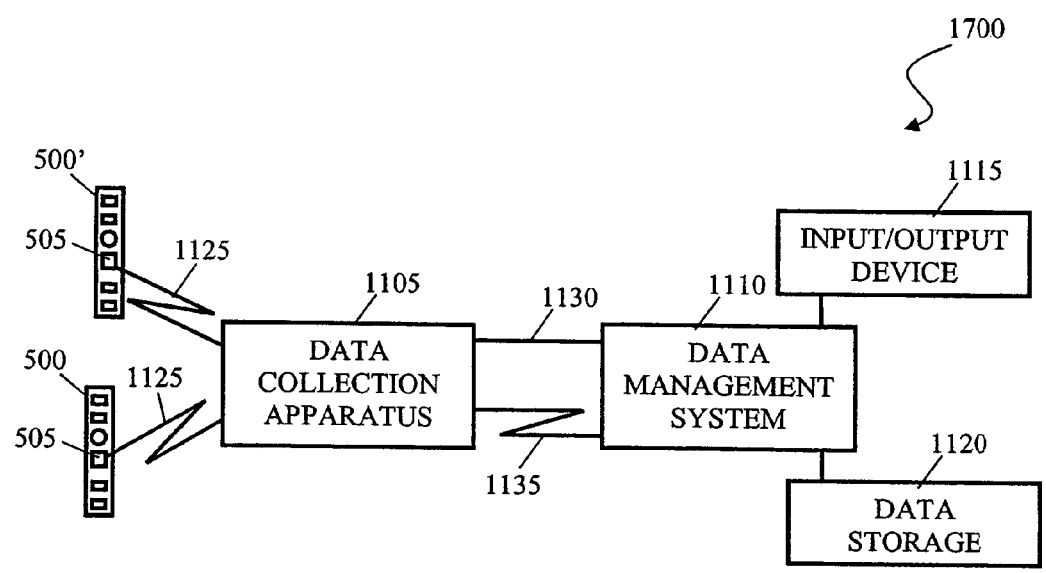
FIG. 17 shows another system for monitoring the hydration of an organism.

FIG. 17 shows an implementation of a system that uses multiple probes for monitoring the hydration of an organism, namely a system 1700. In addition to one or more data collection apparatus 1105, data management system 1110, input/output device 1115, and data storage device 1120, system 1700 includes probes 500, 500'. Probes 500, 500' can be deployed on a single organism 405 as shown in FIG. 16. Probes 500, 500' can both establish wireless data links 1125 with data collection apparatus 1105 to communicate information used in hydration monitoring.

Accordingly, other implementations are within the scope of the following claims.

What is claimed is:

1. A method comprising:
   affixing a portable probe dimensioned and configured to be continuously affixed to an ambulatory subject on a selected area of said subject over a selected time period;
   monitoring a local bioelectric impedance of a portion of said subject using said portable probe, the portable probe exchanging energy with the portion of the subject while affixed to generate impedance data representing at least in part a fluid state of said portion over the selected time period;
   processing said impedance data to derive one or more long term impedance variations representing changes in hydration which occur over a period of at least several hours during said selected time period, and to identify reproducible long term variations in hydration that arise from predictable or habitual patterns not associated with disease states; and
   adjusting subsequent measurement results to account for the identified long term variations in hydration;
   detecting a disease state of said subject associated with a hydration change in said portion of said subject by analyzing at least some adjusted measurement results; and
   providing an indication that a disease state is present.

2. The method of claim 1, wherein the portable probe exchanges energy substantially continuously with the portion of the organism to generate the impedance data.

3. The method of claim 1, additionally comprising transmitting one or more identifiers identifying an electrode, a patch, and/or other electronics of the portable probe to a remote apparatus.

4. The method of claim 1, additionally comprising transmitting a plurality of identifiers to a remote apparatus.

5. The method of claim 1, comprising placing the probe on the thigh of a subject.

6. The method of claim 1, comprising placing the probe on the chest of a subject.

7. The method of claim 6, additionally comprising diagnosing pulmonary edema using said impedance data.

8. The method of claim 1, comprising monitoring bioelectric impedance for a period sufficient to identify a hydration trend over time.

9. The method of claim 1, additionally comprising automatically providing a recommendation for intervention to alleviate a hydration condition.

10. The method of claim 1, comprising communicating the data representing a result of the hydration monitoring to a remote apparatus configured to receive the data from the portable probe.

11. The method of claim 10, comprising wirelessly communicating the data representing a result of the hydration monitoring to a remote apparatus configured to receive the data from the portable probe.

12. The method of claim 10, comprising performing additional data analysis in said remote apparatus.

13. The method of claim 12, comprising performing comparisons between monitoring results to predict future hydration monitoring results.

14. The method of claim 1, comprising monitoring additional bioparameters.

15. The method of claim 14, wherein said additional bioparameters comprise respiration.

16. The method of claim 14, wherein said additional bioparameters comprise heart rate.

17. The method of claim 14, wherein said additional bioparameters comprise hormone and/or metabolite levels.

18. The method of claim 1, comprising placing a plurality of probes on said subject to monitor hydration of said subject.

19. The method of claim 1, comprising comparing/correlating impedance measurements made with said portable probe to other periodically collected biological parameters.

20. The method of claim 19, wherein said periodically collected biological parameters comprise bioelectric impedance.

21. The method of claim 1, wherein said long term variations occur over a period of at least several hours.

22. The method of claim 1, wherein said long term variations comprise diurnal or monthly variations.

23. The method of claim 1, wherein the hydration change comprises detecting a deviation from a baseline.

24. The method of claim 1, wherein the impedance data provides information regarding the amount of fluid within the subject.

* * * * *